US012685870B2

(12) United States Patent
Arfin et al.

(10) Patent No.: US 12,685,870 B2
(45) Date of Patent: Jul. 21, 2026

(54) APPARATUSES AND METHODS FOR TIMING-BASED POWER LEVEL CONTROL

(71) Applicant: Advanced Bionics AG, Staefa (CH)

(72) Inventors: Scott Kenneth Arfin, Valencia, CA (US); R. Tissa Karunasiri, Valencia, CA (US); Glen A. Griffith, Newbury Park, CA (US); Aniket Kulkarni, Vasind-E (IN)

(73) Assignee: Advanced Bionics AG, Staefa (CH)

( * ) Notice: Subject to any disclaimer, the term of this patent is extended or adjusted under 35 U.S.C. 154(b) by 365 days.

(21) Appl. No.: 18/561,148

(22) PCT Filed: Jun. 11, 2021

(86) PCT No.: PCT/US2021/037062
§ 371 (c)(1),
(2) Date: Nov. 15, 2023

(87) PCT Pub. No.: WO2022/260683
PCT Pub. Date: Dec. 15, 2022

(65) Prior Publication Data
US 2024/0278023 A1     Aug. 22, 2024

(51) Int. Cl.
*A61N 1/37* (2006.01)
*A61N 1/02* (2006.01)
(Continued)

(52) U.S. Cl.
CPC ......... *A61N 1/37276* (2013.01); *A61N 1/025* (2013.01); *A61N 1/0541* (2013.01);
(Continued)

(58) Field of Classification Search
CPC .. A61N 1/025; A61N 1/0541; A61N 1/36038; A61N 1/37217; A61N 1/37223;
(Continued)

(56) References Cited

U.S. PATENT DOCUMENTS 6,073,050 A    6/2000  Griffith
7,016,738 B1   3/2006  Karunasiri
(Continued)

OTHER PUBLICATIONS

International Search Report and Written Opinion received in International Application No. PCT/US2021/037062 on Mar. 1, 2022.

*Primary Examiner* — Amanda K Hulbert
(74) *Attorney, Agent, or Firm* — ALG Intellectual Property, LLC

(57) ABSTRACT

An illustrative timing-based power control apparatus includes a signal generation circuit and a power control circuit. The signal generation circuit is configured to generate a carrier signal for wireless transmission of output power and output data, the carrier signal associated with a first fundamental component having a particular frequency, a particular phase, and a first amplitude. The power control circuit is configured to generate a time-adjusted version of the carrier signal that maintains an amplitude of the carrier signal and adjusts a timing profile of the carrier signal such that a second fundamental component associated with the time-adjusted version of the carrier signal has the particular frequency, the particular phase, and a second amplitude lower than the first amplitude. The second amplitude may be associated with a target power level for the output power of the wireless transmission. Corresponding systems and methods are also disclosed.

13 Claims, 12 Drawing Sheets

(51) Int. Cl.

| | |
|---|---|
| *A61N 1/05* | (2006.01) |
| *A61N 1/36* | (2006.01) |
| *A61N 1/372* | (2006.01) |
| *A61N 1/378* | (2006.01) |

(52) U.S. Cl.
CPC ..... *A61N 1/36038* (2017.08); *A61N 1/37217* (2013.01); *A61N 1/3727* (2013.01); *A61N 1/3787* (2013.01)

(58) Field of Classification Search
CPC .............. A61N 1/3727; A61N 1/37276; A61N 1/3787; H04L 27/02
See application file for complete search history.

(56) References Cited

U.S. PATENT DOCUMENTS

| | | | | |
|---|---|---|---|---|
| 8,275,462 | B1 | 9/2012 | Griffith | |
| 10,258,803 | B2 | 4/2019 | Palmer et al. | |
| 2016/0044427 | A1* | 2/2016 | Meskens .............. | H04R 25/606 |
| | | | | 381/312 |
| 2017/0207659 | A1* | 7/2017 | Mofidi .................... | H04B 5/79 |
| 2020/0057462 | A1 | 2/2020 | Karunasiri et al. | |

* cited by examiner

APPARATUSES AND METHODS FOR TIMING-BASED POWER LEVEL CONTROL

BACKGROUND INFORMATION

Various types of medical systems and devices include external and implanted components that are coupled together during operation. As one example, people who have little or no natural hearing may benefit from a cochlear implant system that stimulates auditory nerves in ways that natural hearing mechanisms fail to stimulate for various reasons. A cochlear implant system may include external components such as a microphone for capturing an audio signal, a sound processor for generating stimulation parameters based on the audio signal, and a headpiece for wirelessly transmitting power and data associated with the stimulation parameters to a cochlear implant that applies electrical stimulation to a recipient of the cochlear implant system. In this example, the cochlear implant may include an electrode lead that has been inserted into a cochlea of the recipient and may wirelessly receive the power and data from the external components (e.g., the headpiece) and use this power and data to apply the desired electrical stimulation to the cochlea by way of the electrode lead. Other types of implanted medical devices and systems may operate in similar ways, with power and data similarly being transmitted wirelessly (i.e., transcutaneously) through the skin.

For any of these types of systems, it is desirable for power and data transmission to be efficient so as to minimize wasted power, extend battery life, reduce heat dissipation, and so forth. In certain examples, it would be desirable to gain such efficiencies using circuitry that is as unobtrusive (e.g., small, light, etc.) as possible. Unfortunately, conventional techniques for controlling power levels involve electrical components (e.g., buck converter circuits and associated passive elements such as capacitors and inductors, etc.) that tend to be relatively large, bulky, heavy, power-hungry, and/or otherwise unconducive to these and other design goals for the system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
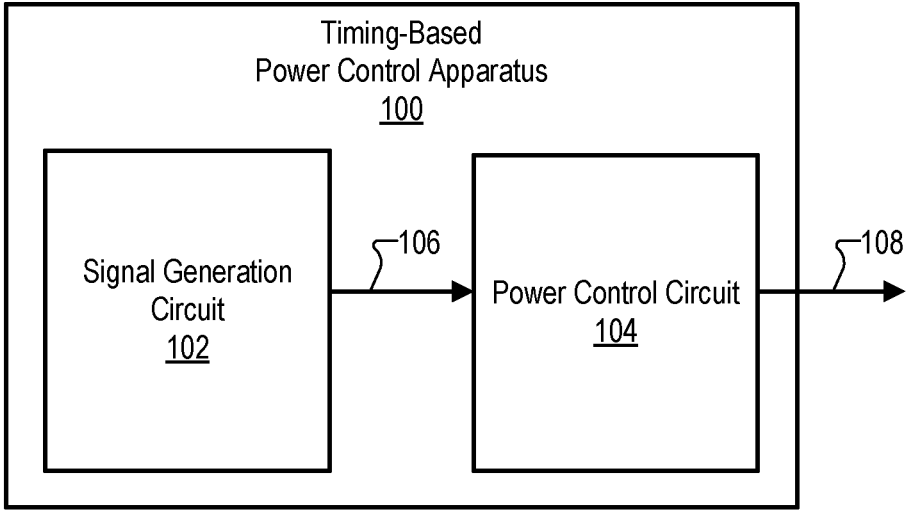
FIG. 1 shows an illustrative timing-based power control apparatus configured to perform timing-based power level control.

Apparatuses and methods for timing-based power level control are described herein. As described above, medical systems and devices (e.g., cochlear implant systems and/or other medical systems and devices that handle power and data transfer in similar ways) may include one or more external components and one or more internal (implanted) components. The external components may be configured to generate and wirelessly transmit power and data for the implanted components to receive and use to accomplish the purposes of the medical device or system. For example, a headpiece may wirelessly transmit, to a cochlear implant device implanted within a recipient, a carrier signal that carries radio frequency (RF) power (e.g., power to be used by the cochlear implant to apply electrical stimulation to the recipient) as well as modulated stimulation data (e.g., data representative of stimulation parameters dictating how the electrical stimulation is to be applied).

As power and data are wirelessly transmitted in these types of systems, it may be desirable for the wireless transfer to be performed efficiently for various reasons described above. For example, it may be desirable to consistently provide enough power for the implanted component to be able to operate properly (e.g. to provide the appropriate amount of stimulation to the recipient, etc.) while, at the same time, not providing so much power that a significant amount of the power is wasted. One way to control the power level of a wireless transmission is to use an efficient RF power supply to generate and/or modulate the carrier signal at a particular voltage that provides a desired amount of power. For instance, a buck converter integrated circuit (IC) configured to control the voltage level of the carrier signal may be employed for this purpose. Unfortunately, as mentioned above, such ICs may require design compromises (e.g., due to the size or bulkiness of the ICs, the power they consume, etc.) and/or may be implemented with other devices (e.g., passive elements such as large capacitors, inductors, resistors, etc.) that themselves require such compromises.

To address these challenges, systems and methods described herein provide timing-based power level control so that voltage-based power level controllers (e.g., the buck converter IC described above or similar power supplies) and their associated passive elements may be eliminated or simplified, thereby reducing the size, weight, power consumption, and other such characteristics of the external parts of the system. As will be described in more detail below, timing-based power level control may operate by adjusting a timing profile of the carrier signal rather than a voltage profile of the signal. For example, while a voltage level of the carrier signal may remain at a particular level, the timing profile may be adjusted (e.g., by skipping pulses, by shortening pulses, or by other techniques described herein) in a manner that reduces the power level being transmitted while keeping the fundamental phase and frequency of the carrier signal the same. Methods and systems for timing-based power level control may function to transfer power alone, or may produce time-adjusted carrier signals onto which data is modulated (in various ways described herein) so as to transfer power and data together.

Systems and methods described herein may employ timing-based power level control as an alternative to, or in combination with, conventional voltage-based power level control, and in doing so may provide various benefits and advantages. As one example that was mentioned above, timing-based power level control mechanisms may allow certain power supply circuitry to be reduced, simplified, or even eliminated altogether. In many cases, this may improve battery life for the system; may allow the system to run cooler and more efficiently (since less power is wasted and less heat is generated); may allow external component design (e.g., headpiece design) to have more desirable characteristics for recipients (e.g., lighter, smaller, more inconspicuous, etc.); may reduce system costs; and may otherwise augment or improve the system characteristics. Other benefits may include reduced design time, more flexible products that may be updated in the field using software (e.g., to program new types of timing profiles to be used) rather than requiring hardware updates (which may be difficult or impractical to deploy after the product is released), facilitation of active and/or fully-integrated external components (e.g., headpieces that include power generation circuitry and/or sound processing circuitry rather than that circuitry being implemented in a separate sound processor component), and so forth.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Systems and methods described herein for timing-based power level control may provide any of the benefits mentioned above, as well as various additional and/or alternative benefits that will be described and/or made apparent below.

FIG. 1 shows an illustrative timing-based power control apparatus 100 ("apparatus 100") that is configured to perform timing-based power level control in accordance with principles described herein. As will be described and illustrated in more detail below, apparatus 100 may be implemented as part of any suitable system or device to facilitate effective and efficient performance by that system or device. As one example, apparatus 100 may be included in an external component (e.g., a headpiece, etc.) of a medical system (e.g., a cochlear implant system) that operates using wireless transfer of power and/or data between the external component and an internal component (e.g., an implanted component such as a cochlear implant). Apparatus 100 may include any suitable circuitry to perform operations described herein. For example, power supply circuitry (e.g., RF power generators, etc.), passive circuitry (e.g., resistors, capacitors, inductors, etc.), logic circuitry (e.g., individual gates, combinatorial logic, etc.), memory or storage circuits (e.g., flip flops, solid-state memory, etc.), and/or more complex circuitry (e.g., microprocessors, field programmable gate arrays (FPGAs), application specific integrated circuits (ASICs), etc.), may all be used to implement apparatus 100 in various cases as may serve a particular implementation.

As shown, apparatus 100 may include a signal generation circuit 102 (e.g., signal generation circuitry implemented by any of the circuitry described above) and a power control circuit 104 (e.g., power control circuitry implemented by any of the circuitry described above) that are communicatively coupled to one another. As will be described in more detail below, signal generation circuit 102 may be configured to generate a carrier signal 106 for wireless transmission of output power and output data, while power control circuit 104 may be configured to generate a time-adjusted version 108 of carrier signal 106. Time-adjusted version 108 of carrier signal 106 may also be referred to herein as time-adjusted carrier signal 108, but it will be understood that this time-adjusted version of carrier signal 106 is generated based on carrier signal 106 and is thus related to carrier signal 106 in various ways (e.g., having the same voltage profile, fundamental frequency, and fundamental phase, but having a different timing profile and different fundamental amplitude so as to carry less power).

As one example of the relationship between carrier signal 106 and time-adjusted carrier signal 108, carrier signal 106 may be associated with a first fundamental component having a particular frequency, a particular phase, and a first amplitude. This fundamental component may be a sinusoidal signal that is combined with various other sinusoidal signals (harmonic components, overtone components, etc.) to form carrier signal 106. The first amplitude of the fundamental component of carrier signal 106 may be associated with a maximum supported power level for the output power that apparatus 100 generates as part of the wireless transmission. However, apparatus 100 may also receive timing control data (not explicitly shown in FIG. 1) that corresponds to a target power level for the output power that is lower than the maximum supported power level for the output power. Based on this timing control data, time-adjusted carrier signal 108 may be generated to maintain an amplitude of the carrier signal, but to have an adjusted timing profile as compared to carrier signal 106. For example, while carrier signal 106 may include a series of pulses generated at the particular frequency of the first fundamental component (e.g., forming a square wave with a 50% duty cycle), the timing profile of these pulses may be altered for time-adjusted carrier signal 108 such as by periodically skipping pulses, altering the duty cycle of the pulses in certain ways, and so forth.

As a result of the timing profile changes from carrier signal 106 to time-adjusted carrier signal 108, a second fundamental component associated with time-adjusted carrier signal 108 may have the same particular frequency and the same particular phase as carrier signal 106, but may have a second amplitude that is different than the first amplitude of the first fundamental component. Specifically, the second amplitude of the second fundamental of time-adjusted carrier signal 108 may be lower than the first amplitude and may be associated with the target power level for the output power (based on the timing control data). In order to preserve the frequency and phase of the first fundamental component while reducing the amplitude as the timing profile is adjusted, systems and methods described herein disclose methods for symmetrically shortening certain pulses from a series of pulses that may be included in carrier signal 106. As used herein, a pulse is "symmetrically shortened" when the duty cycle of the pulse is changed in a way that symmetrically moves the rising edge and the falling edge of a pulse inward toward one another by equal amounts or at an equal rate such that zero crossings of the fundamental component (and therefore the phase of the fundamental component) are preserved and maintained. Examples of symmetric shortening of pulses and illustrative ways in which this may be accomplished will be described in more detail below.

It will be understood that various advantages may arise from being able to reduce the amplitude of the fundamental component of the carrier signal while maintaining the frequency and phase of the carrier signal in the ways described herein. For example, if all the telemetry data (or all the telemetry data in a certain direction such as from the external component to the internal component of a medical system such as a cochlear implant system) is to be transmitted at a single frequency (e.g., a frequency for which legal authorization has been obtained from regulatory agencies or the like), it may be important for frequency and phase to remain consistent even if the fundamental amplitude (representative of the power level being transmitted by way of the carrier signal) is adjusted.

Figure 2:
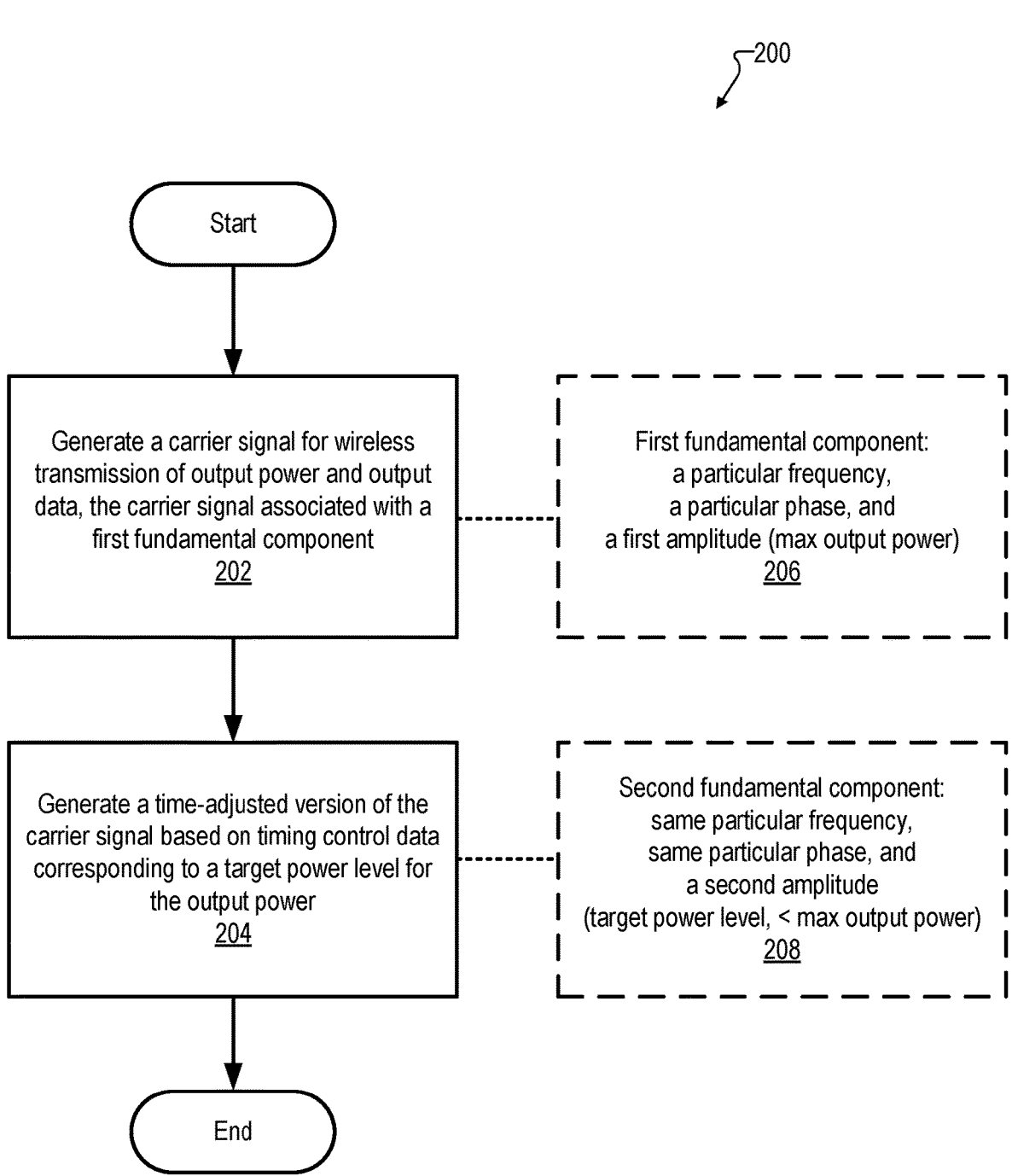
FIG. 2 shows an illustrative method for timing-based power level control.

FIG. 2 shows an illustrative method 200 for timing-based power level control in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 or described in relation to FIG. 2 may be performed concurrently (e.g., in parallel) with one another, rather than being performed sequentially as illustrated and/or described. One or more of the operations shown in FIG. 2 may be performed by a timing-based power control apparatus such as apparatus 100 and/or any implementation thereof. For instance, method 200 may be performed by a headpiece of a cochlear implant system or other similar external component of another type of medical system described herein, or by other suitable systems or devices as may serve a particular implementation.

In some examples, the operations of FIG. 2 may be performed in real time so as to provide, receive, process, and/or use signals and data described herein immediately as the signals (or data) are generated, updated, changed, exchanged, or otherwise become available. Moreover, certain operations described herein may involve real-time signals, real-time representations, real-time conditions, and/or other real-time circumstances. As used herein, "real time" will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time signals, real-time data, real-time representations, real-time conditions, and so forth, will be understood to refer to data, representations, and conditions that relate to a present moment in time or a moment in time when decisions are being made and operations are being performed (e.g., even if after a short delay), such that the signals, data, representations, conditions, and so forth are temporally relevant to the decisions being made and/or the operations being performed.

Each of operations 202 and 204 of method 200, along with certain conditions 206 and 208 that may be associated with these operations, will now be described in more detail as the operations may be performed by circuitry included within a timing-based power control apparatus (e.g., apparatus 100 or an implementation thereof) or another suitable system or device.

At operation 202, a signal generation circuit (e.g., signal generation circuit 102) included in a timing-based power control apparatus (e.g., apparatus 100) may generate a carrier signal (e.g., carrier signal 106) for wireless transmission of output power and output data. As indicated by condition 206 (drawn with dashed lines and connected to operation 202 to indicate that condition 206 arises from or is otherwise associated with the performance of operation 202), the carrier signal generated at operation 202 may be associated with a first fundamental component having a particular frequency, a particular phase, and a first amplitude. As described above in relation to the first fundamental component of carrier signal 106, the first amplitude of the first component may be associated with a maximum supported power level for the output power (indicated as "max output power" in FIG. 2). For example, the maximum supported power level may be a power level that would be transmitted if carrier signal 106 was transmitted as a series of pulses with a 50% duty cycle (a square wave signal rather than a time-adjusted signal in which the timing profile is changed by skipping pulses, shortening pulses to less than 50% duty cycle, or the like).

At operation 204, a power control circuit (e.g., power control circuit 104) included in the timing-based power control apparatus may generate a time-adjusted version of the carrier signal (e.g., time-adjusted carrier signal 108) based on timing control data corresponding to a target power level for the output power. For example, the timing adjusted version of the carrier signal may correspond to a target power level that is lower than the maximum supported power level for the output power and that is configured to help optimize system efficiency in any of the ways described herein.

As indicated by condition 208 (drawn with dashed lines and connected to operation 202 to indicate that condition 208 arises from or is otherwise associated with the performance of operation 204), the time-adjusted version of the carrier signal generated at operation 204 may be associated with a second fundamental component having a same particular frequency and a same particular phase as the first fundamental component described in condition 206, but may have a second amplitude that is different. Specifically, as described above in relation to the second fundamental component of time-adjusted carrier signal 108, the second amplitude of the second fundamental component may be associated with a target power level that is less than the maximum supported power level for the output power (indicated as "target power level<max output power" in FIG. 2). For example, the target power level may be a power level that provides sufficient power to an internal component (e.g., a cochlear implant, etc.) without undue inefficiencies such as have been described. In other words, at operation 204, condition 208 shows that the time-adjusted version of the carrier signal may maintain an amplitude of the carrier signal while adjusting a timing profile of the carrier signal such that the second fundamental component associated with the time-adjusted version of the carrier signal has the particular frequency, the particular phase, and the second amplitude lower than the first amplitude and associated with the target power level for the output power.

Figure 3:
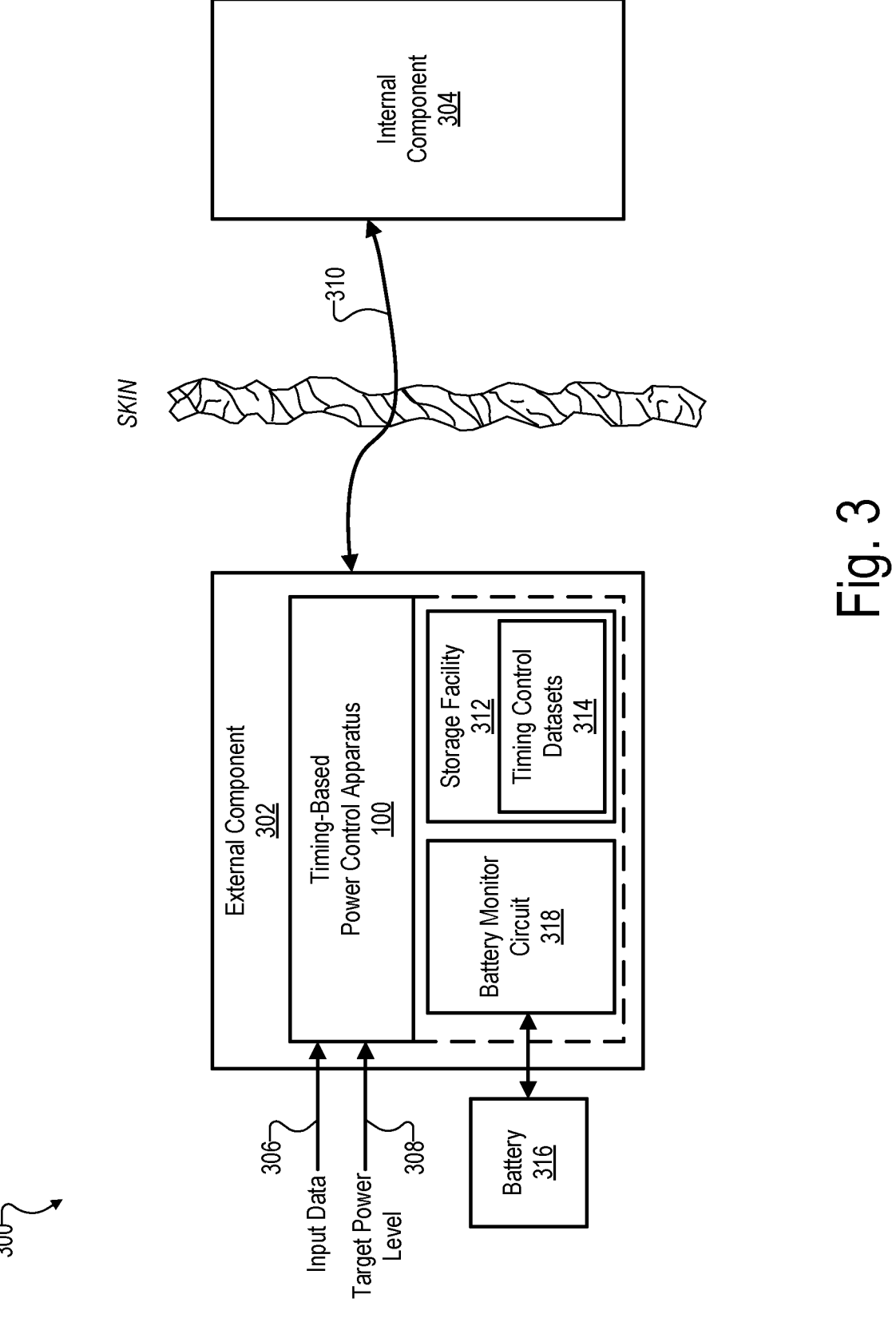
FIG. 3 shows an illustrative configuration within which the apparatus of FIG. 1 may operate to perform timing-based power level control.

FIG. 3 shows an illustrative configuration 300 within which apparatus 100 may operate to perform timing-based power level control in accordance with principles described herein. Specifically, as shown, apparatus 100 is included within an external component 302 that is separated from an internal component 304 by a layer of skin, since internal component 304 may be implanted within a recipient while external component 302 remains external to the recipient. Within external component 302, apparatus 100 may receive input data 306 that is to be transmitted (e.g., along with wireless RF power) to internal component 304, as well as data input representative of a target power level 308 that is to be provided by external component 302 to internal component 304. External component 302 may provide, through the skin of the recipient to be received at internal component 304, a wireless transmission 310 that includes output data (e.g., the same data as input data 306) modulated onto a time-adjusted version of a carrier signal (e.g., a carrier signal that provides power at the designed target power level 308).

To adjust the timing profile of a default carrier signal to generate a time-adjusted version of the carrier signal that will provide target power level 308, external component 302 is shown to include a storage facility 312 that includes, possibly among other data, timing control data packaged into one or more timing control datasets 314. Additionally, a battery 316 is shown to provide battery power (wired direct current (DC) power) to external component 302 and battery monitor circuit 318 is shown to monitor the power level that is provided by battery 316 as that power level may change as the battery is consumed and recharged. A dashed line extending from apparatus 100 to encompass storage facility 312 and battery monitor circuit 318 is shown to indicate that these components may be included within apparatus 100 in certain implementations while, in other implementations, they may be part of external component 302 but considered to be separate from apparatus 100. Additionally, it will be understood that battery 316 may be included within external component 302 and/or apparatus 100 in certain implementations, while being part of a separate external component in other implementations (e.g., included within a separate sound processor in an example in which external component 302 is implemented by a headpiece coupled to the sound processor). Each of the elements 302-318 of configuration 300 will now be described in more detail with reference to FIGS. 3 and 4.

External component 302 and internal component 304 may be any suitable components of a medical system or other stimulation system that operates with certain parts external to a recipient and other parts that are implanted. Such systems may be configured to provide various types of stimulation to the heart, the brain or spinal cord (or other segments of the nervous system), a particular muscle or muscle group, a sensory organ (e.g., the eyes or ears, etc.), or the like. For example, the stimulation system incorporating external component 302 and internal component 304 may be implemented as a hearing system (e.g., a cochlear implant system that provides electrical stimulation to a cochlea of the recipient, an electroacoustic stimulation hearing system that provides a combination of electrical and acoustic stimulation to the recipient, another type of hearing system that provides vibrotactile bone conduction or other stimulation to the recipient, etc.), a neuromodulation system (e.g., a spinal cord stimulator, a sacral stimulator, etc.), or another suitable stimulation system (e.g., a cardiac pacemaker, etc.).

Figure 4:
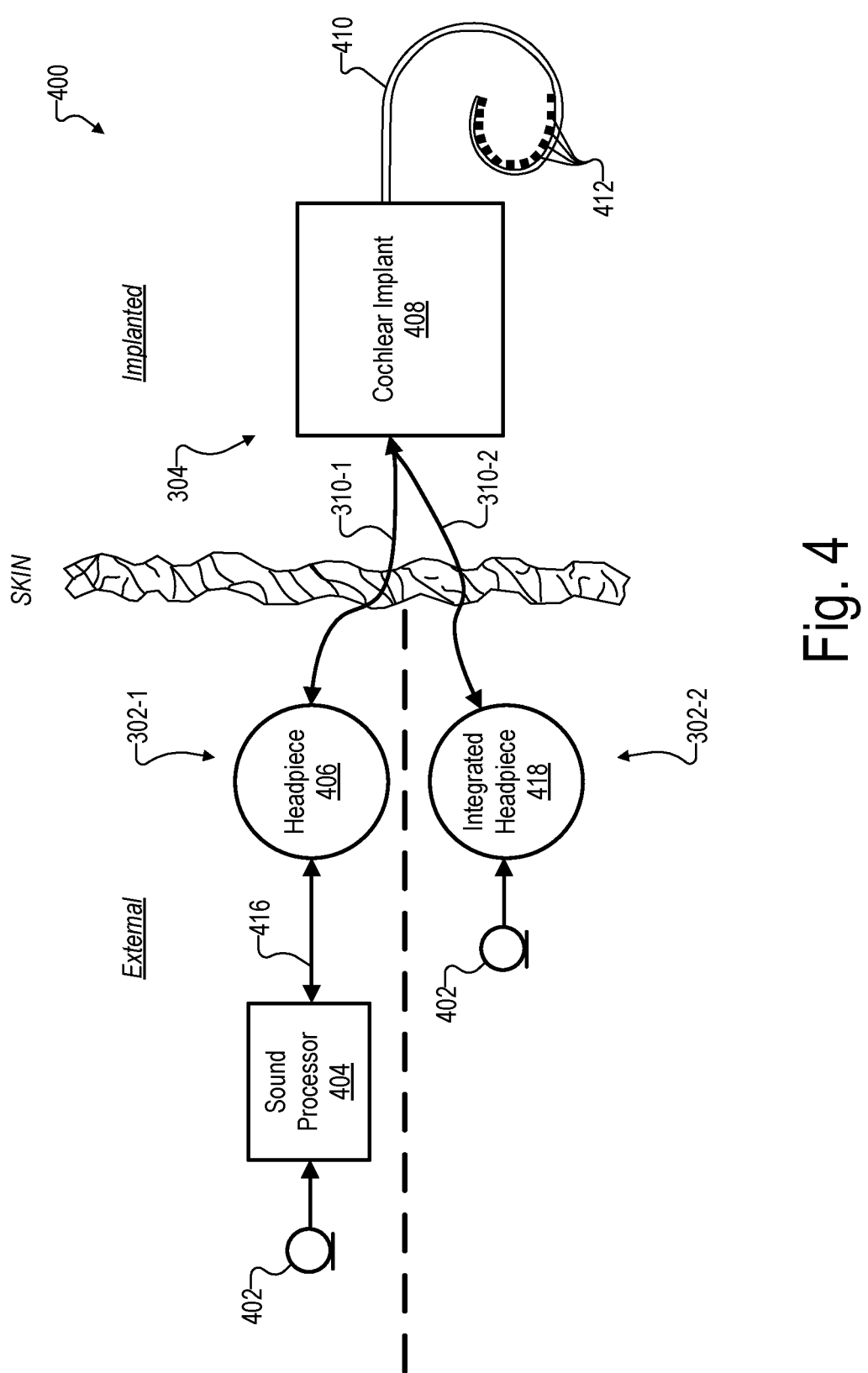
FIG. 4 shows how an illustrative cochlear implant system may implement the configuration of FIG. 3.

To provide a more specific example of a stimulation system that may implement configuration 300, FIG. 4 shows an illustrative cochlear implant system that may implement configuration 300. Specifically, in this example, apparatus 100 may be implemented within an external headpiece included in a cochlear implant system that further includes an internal cochlear implant configured to receive a wireless transmission of output power and output data from the external headpiece when the internal cochlear implant is implanted within a recipient of the cochlear implant system and the external headpiece is external to the recipient.

FIG. 4 shows an exemplary cochlear implant system 400 in which two alternative external component scenarios (separated by a dashed line) are illustrated external to the skin ("External"), while a cochlear implant is illustrated internal to the skin ("Implanted"). Referring first to the scenario above the dashed line, cochlear implant system 400 is shown to include, in this implementation, a microphone 402, a sound processor 404, and a headpiece 406 that are external to the skin of the recipient and communicatively coupled to a cochlear implant 408 implanted within the recipient. Cochlear implant 408 is shown to be coupled with an electrode lead 410 having a plurality of electrodes 412. In this first implementation, an arrow labeled "302-1" indicates that external component 302 is to be understood to be implemented by headpiece 406, while an arrow labeled "304" indicates that internal component 304 is to be understood to be implemented by cochlear implant 408. Additionally, as shown, wireless transmission 310 between headpiece 406 and cochlear implant 408 is represented by a connection labeled "310-1" for the first implementation.

Microphone 402 is configured to detect one or more audio signals (e.g., that include speech and/or any other type of sound) in an environment of the recipient. Microphone 402 may be implemented in any suitable manner. For example, microphone 402 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 404. Additionally or alternatively, microphone 402 may be implemented by one or more microphones in or on headpiece 406, one or more microphones in or on a housing of sound processor 404, one or more beam-forming microphones, and/or any other suitable microphone as may serve a particular implementation.

Sound processor 404 may be implemented by any suitable device that may be worn or carried by the recipient. For example, sound processor 404 may be implemented by a behind-the-ear (BTE) unit configured to be worn behind and/or on top of an ear of the recipient. Additionally or alternatively, sound processor 404 may be implemented by an off-the-ear unit (also referred to as a body worn device) configured to be worn or carried by the recipient away from the ear.

In certain examples, headpiece 406 may be implemented as a passive headpiece that receives, by way of a communication link 416 (implemented by a cable or the like), a modulated RF signal from sound processor 404. In other examples, headpiece 406 may be implemented as an active headpiece that receives, by way of communication link 416, DC power and a baseband data signal. In the passive example, headpiece 406 may wirelessly transmit, to cochlear implant 408, the modulated RF signal received from sound processor 404, while, in the active example, headpiece 406 may both generate and transmit such a modulated RF signal based on the DC power and data signal received from sound processor 404.

In either case, headpiece 406 may include an external antenna (e.g., a coil and/or one or more wireless communication components) configured to facilitate selective wireless coupling of sound processor 404 to cochlear implant 408. Headpiece 406 may additionally or alternatively be used to selectively and wirelessly couple any other external device to cochlear implant 408. To this end, headpiece 406 may be configured to be affixed to the recipient's head and positioned such that the external antenna housed within headpiece 406 is communicatively coupled to a corresponding implantable antenna (which may also be implemented by a coil and/or one or more wireless communication components) included within or otherwise connected to cochlear implant 408. In this manner, input data (e.g., stimulation parameters, etc.) and/or power signals may be wirelessly and transcutaneously transmitted between sound processor 404 and cochlear implant 408 by way of wireless transmission 310-1.

In operation, sound processor 404 may receive an audio signal detected by microphone 402 by receiving a signal (e.g., an electrical signal) representative of the audio signal from microphone 402. Sound processor 404 may additionally or alternatively receive the audio signal by way of any other suitable interface as described herein. Sound processor 404 may process the audio signal in any of the ways described herein and transmit, by way of headpiece 406, stimulation parameters and power to cochlear implant 408 to direct cochlear implant 408 to apply electrical stimulation representative of the audio signal to the recipient by way of electrodes 412 on electrode lead 410. For example, the stimulation parameters may be generated and provided in accordance with a particular sound processing program (e.g., program strategy) configured to account for particular conditions of the hearing environment, particular attributes and/or preferences of the recipient, and so forth.

An alternative implementation of cochlear implant system 400 is shown with different components below the dashed line on the external side of the skin. Specifically, in this case, the external headpiece may be implemented as an integrated headpiece 418 or "one-piece system" that includes, together with a signal generation circuit and a power control circuit such as have been described, a sound processing circuit configured to perform the functionality described above for sound processor 404. For example, in contrast to the first implementation including the separate sound processor 404, integrated headpiece 418 of this second implementation may be configured to generate, based on input audio data from a similar microphone 402, the output data wirelessly transmitted to the cochlear implant by way of wireless transmission 310 (labeled as wireless transmission 310-2 in this second implementation to distinguish from wireless transmission 310-1 of the first implementation). As shown by a reference designator "302-2," integrated headpiece 418 may be considered to be an alternative implementation of external component 302 that may be used instead of headpiece 406.

In certain examples, integrated headpiece 418 may include one or more embedded microphones implementing microphone 402, a battery and associated power circuitry, and any other external circuitry used by cochlear implant system 400. In other examples, the sound processing circuitry and power/data transmission circuitry (e.g., including apparatus 100) may be included within integrated headpiece 418 while a battery, microphone, and/or other components may still be housed separately from integrated headpiece 418 (e.g., within a BTE external component or other such device). In either of these examples, as well as the example of the active implementation of headpiece 406 described above, it may be advantageous for RF power to not be transferred between a sound processor and a headpiece, as such transmission may generate unwanted emissions, cause unwanted power consumption, or otherwise be undesirable. However, it has conventionally be challenging to implement an integrated and/or active headpiece (such as the active implementation of headpiece 406 or integrated headpiece 418) in part because of the weight and size of power circuitry that operates in the conventional ways mentioned above (e.g., using buck converters and associated passive elements to provide voltage-based power level control, etc.). Accordingly, methods and systems described herein for timing-based power level control that allow for weight and size of an active and/or integrated headpiece to be reduced may be especially advantageous for these implementations.

In either the first or second implementations of cochlear implant system 400 illustrated in FIG. 4, cochlear implant system 400 will be understood to implement a medical system or other stimulation system such as described above in relation to configuration 300. In both implementations, the cochlear implant system will be understood to include: 1) a headpiece (e.g., headpiece 406 or integrated headpiece 418) configured to be worn externally by a recipient of the cochlear implant system and to provide a wireless transmission (e.g., wireless transmission 310-1 or 310-2) of output power and output data; 2) a cochlear implant (e.g., cochlear implant 408) configured to be implanted within the recipient and to receive the wireless transmission from the headpiece; 3) a signal generation circuit (not explicitly shown in FIG. 4) included within the headpiece and configured to generate a carrier signal for the wireless transmission, the carrier signal associated with a first fundamental component having a particular frequency, a particular phase, and a first amplitude associated with a maximum supported power level for the output power; and 4) a power control circuit (not explicitly shown in FIG. 4) included within the headpiece and configured to generate, based on timing control data corresponding to a target power level for the output power that is lower than the maximum supported power level for the output power, a time-adjusted version of the carrier signal that maintains an amplitude of the carrier signal and adjusts a timing profile of the carrier signal such that a second fundamental component associated with the time-adjusted version of the carrier signal has the particular frequency, the particular phase, and a second amplitude lower than the first amplitude and associated with the target power level for the output power.

Returning to FIG. 3, input data 306 may include any data that is to be transmitted to internal component 304 for a particular implementation. For instance, in the cochlear implant system example illustrated in FIG. 4, input data 306 may be data representative of stimulation parameters that have been generated by the sound processor and are to be transmitted by the headpiece for use by the cochlear implant in applying stimulation to the recipient. In other examples, input data 306 may be other types of data that are to be transmitted as output data on wireless transmission 310 to internal component 304. In any of these cases, input data 306 may be transmitted by being modulated onto a carrier signal generated and modified (e.g., time adjusted) within apparatus 100 in the ways described herein.

Target power level 308 may be received from any suitable source and may indicate what power level is desirable for external component 302 to provide to internal component 304 under particular circumstances. In certain examples, target power level 308 may be relatively static. For instance, in certain examples, target power level 308 may be based on one or more relatively static factors such as a program strategy used for the wireless transmission of output power and output data (e.g., a sound processing program utilized by the sound processor of a particular implementation of cochlear implant system 400, etc.), a physical distance between external component 302 and internal component 304 when the internal component is implanted within the recipient and the external component is external to the recipient (e.g., based on the thickness of the skin flap of the particular recipient, the exact placement of internal component 304 during the implantation procedure, etc.), or the like. Additionally or alternatively, target power level 308 may account for the current battery level of battery 316, which may stay relatively static but may decrease slowly as battery 316 is consumed and the DC voltage it provides is reduced.

In certain examples, target power level 308 may be adjusted more dynamically based on factors that tend to change more quickly than the width of a skin flap or the voltage level provided by a battery. For instance, in the cochlear implant system example, target power level 308 may vary with a volume of sound in the environment of the recipient (e.g., the magnitude of the audio signal being captured by the microphone) or another such factor that may dynamically change from moment to moment.

Based on input data 306 and target power level 308, apparatus 100 may generate output power and/or output data (e.g., data modulated onto the carrier signal carrying the output power) for wireless transmission 310. Wireless transmission 310 may be transcutaneously provided from external component 302 to internal component 304 in any of the ways that have been described. Additionally, as indicated by the bidirectional nature of the arrow representing wireless transmission 310, it will be understood that wireless transmission 310 may include both a forward telemetry aspect (e.g., RF power and data transmitted from external component 302 to internal component 304) as well as a backward telemetry aspect (e.g., data transmitted from internal component 304 back out to external component 302).

In certain implementations, timing control data configured to implement a particular target power level 308 may be accessed by apparatus 100 as part of generating wireless transmission 310. For example, as will be described and illustrated in more detail below, a timing control dataset may include data that facilitates the adjustment of an original carrier signal to generate the time-adjusted version of the carrier signal in a manner that provides the desired target power level 308 for the output power. Accordingly, a library of potential timing control datasets corresponding to various potential values for target power level 308 may be stored within a storage facility 312 as timing control datasets 314 and apparatus 100 may access a particular timing control dataset 314 based on target power level 308 as apparatus 100 performs operations to generate the time-adjusted version of the carrier signal used for wireless transmission 310.

Storage facility 312 may be configured to maintain the plurality of timing control datasets 314 corresponding to the plurality of different target power levels for the output power, as shown. For a given target power level 308 (e.g., for a given battery level, sound processing program, distance between external component 302 and internal component 304, etc.) the plurality of timing control datasets 314 may include a particular timing control dataset 314 having timing control data corresponding to that target power level 308. As such, part of the generating of the time-adjusted version of the carrier signal performed by apparatus 100 may include selecting and accessing, by the power control circuit, the particular timing control dataset 314 from storage facility 312.

Prior to the selecting and accessing of the particular timing control dataset 314 (and as further part of the generating of the time-adjusted version of the carrier signal), the power control circuit of apparatus 100 may identify target power level 308 for the output power. As mentioned above, this identified target power level 308 may be based on at least one of a program strategy used for the wireless transmission of output power and output data, or a distance between the external and internal components of the medical system when the internal component is implanted within the recipient and the external component is external to the recipient. The power control circuit may select and access the particular timing control dataset 314 from storage facility 312 based on the identified target power level 308.

Additionally or alternatively, as also mentioned above, the timing control data may be changed dynamically based on a detected battery level. For example, as shown in FIG. 3, external component 302 may include a battery monitor circuit 318 that continuously or periodically detects a battery level of battery 316 as battery 316 supplies DC power to the signal generation circuit and the power control circuit of apparatus 100. Based on the battery level detected by battery monitor circuit 318, apparatus 100 may generate the time-adjusted version of the carrier signal differently in order to deliver the desired amount of power. For example, because the amplitude of the carrier signal may decrease as battery 316 is gradually consumed, a different timing profile for the time-adjusted version of the carrier signal may be required at a later time than was used at an earlier time to deliver the same amount of power (i.e., to create a fundamental component of the carrier signal with the same amplitude).

More specifically, the power control circuit of apparatus 100 may be configured to generate the time-adjusted version of the carrier signal based on one timing control dataset 314 when battery monitor circuit 318 detects that the battery level of battery 316 is above a particular threshold. The power control circuit may also be configured to generate the time-adjusted version of the carrier signal based on a different timing control dataset 314 (e.g., a timing control dataset corresponding to a different target power level for the output power) when battery monitor circuit 318 detects that the battery level of battery 316 is below the particular threshold.

FIGS. 5-9 show illustrative aspects of carrier signals and their fundamental components for various implementations of timing-based power level control performed by the apparatus of FIG. 1. More specifically, in each of FIGS. 5-9, signal generation circuit 102 and power control circuit 104 are shown generating carrier signal 106 and time-adjusted carrier signal 108 (the time-adjusted version of carrier signal 106) at the top of the figure, and particular implementations of carrier signal 106, time-adjusted carrier signal 108, and respective first and second fundamental components of these versions of the carrier signal, are illustrated below the signals 106 and 108 in the figure.

Figure 5:
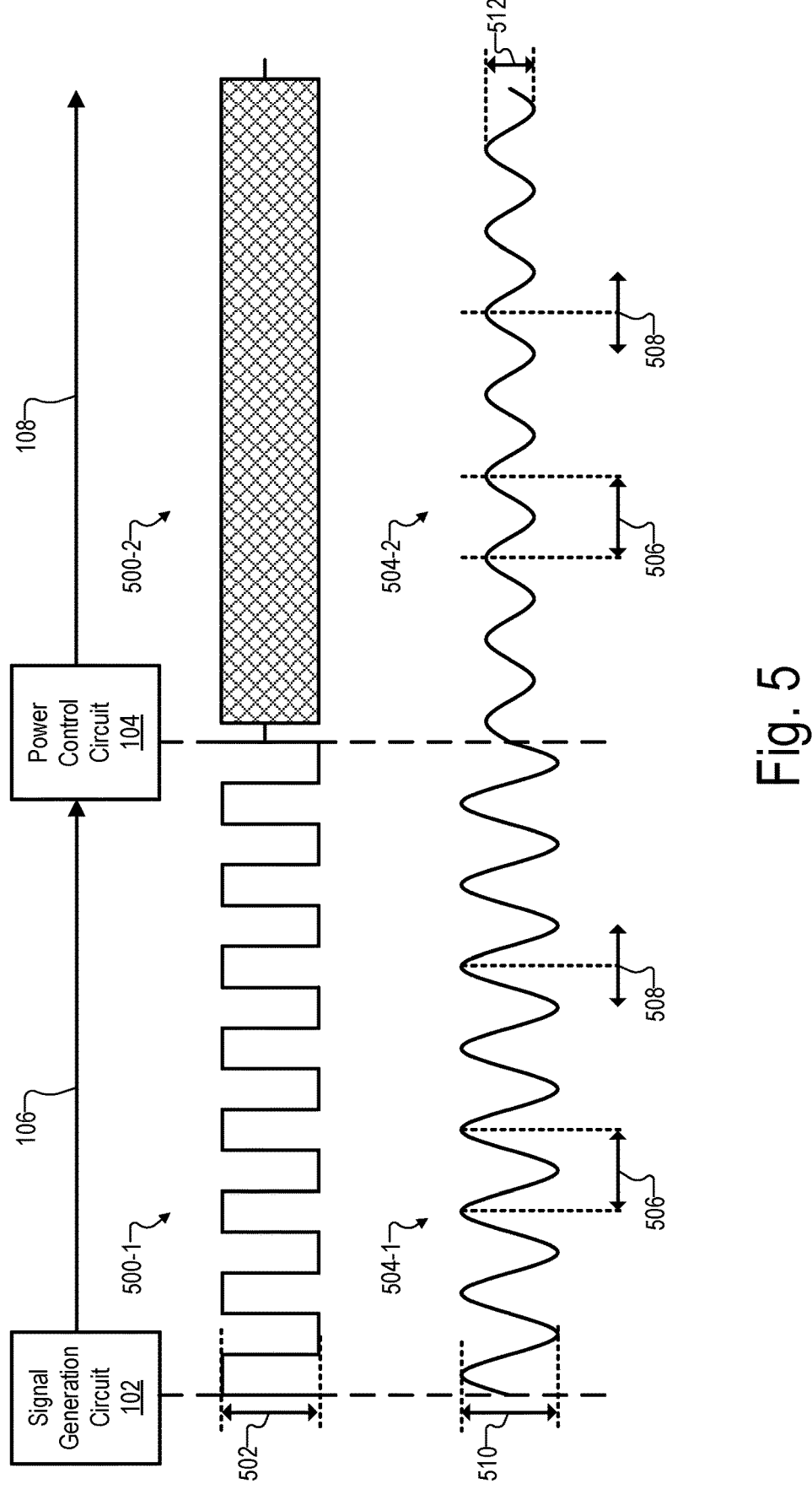
FIGS. 5-9 show illustrative aspects of carrier signals and their fundamental components for various implementations of timing-based power level control performed by the apparatus of FIG. 1.

In FIG. 5, for example, a carrier signal 500-1 implementing carrier signal 106 is shown to include a series of pulses having a particular timing profile. Specifically, as shown, the pulses of carrier signal 500-1 are generated at a particular frequency, generated to have a particular duty cycle (e.g., a 50% duty cycle in this example), and so forth. In this example, the series of pulses making up carrier signal 500-1 form a square wave, which, with its 50% duty cycle, may be configured to carry a maximum amount of power for an amplitude 502 of the carrier signal.

It will be understood that, insofar as amplitude 502 represents the maximum amount of power to be carried by carrier signal 500 (at the 50% duty cycle with no skipped or modified pulses), amplitude 502 refers to the output amplitude of the actual transmitted RF signal. However, for efficiency purposes, it will also be understood that a different amplitude may be employed by apparatus 100 (e.g., by signal generation circuit 102 and/or power control circuit 104) for purposes of generating and time-adjusting the carrier signal, and that the output amplitude 502 may be switched to as a final step prior to outputting wireless transmission 310. For example, all the signal processing involving carrier signal 500-1 and time adjustments to generate time-adjusted carrier signal 500-2 may be performed using low-voltage logic circuits (e.g., operating at 1.0 V in one example) and then, at the output stage, a level shifter may be used to bring the amplitude of the signal up to the full battery or power supply voltage (e.g., 3.6 V in one example).

Additionally, while amplitude 502 is illustrated as being the same for carrier signal 500-1 and for time-adjusted carrier signal 500-2 (thereby illustrating an implementation that may rely exclusively on timing-based power level control), it will be understood that in certain implementations, timing-based power level control may be used in combination with conventional voltage-based power level control. In such implementations, if amplitude 502 is the amplitude of carrier signal 500-1, an amplitude different from amplitude 502 (e.g., less than amplitude 502) may be used for time-adjusted carrier signal 500-2 to increase the potential dynamic range that may be achievable for the total amount of power ultimately delivered, as well as to enhance the controllability of the power level control performed by apparatus 100.

At power control circuit 104, a time-adjusted version of carrier signal 500-1 is generated by adjusting the timing profile of carrier signal 500-1 to generate a time-adjusted carrier signal 500-2 that implements time-adjusted carrier signal 108. While specific changes to the timing profile of a standard square wave carrier signal will be illustrated in FIGS. 6-9 below, the example of FIG. 5 illustrates time-adjusted carrier signal 500-2 as a black box to generically represent any of various changes to the timing profile of the carrier signal that may be made for the time-adjusted version of the carrier signal. For example, as will be described and illustrated in more specific examples below, time-adjusted carrier signal 500-2 may alter the pulses of carrier signal 500-1 by symmetrically shortening certain pulses, skipping certain pulses, doing a combination of these, and/or performing other timing profile adjustments.

As shown, both carrier signal 500-1 and time-adjusted carrier signal 500-2 may have the same amplitude 502, even though, as will be further explained below, these different versions of the carrier signal may carry different amounts of power. As described above, significant benefits may arise from this feature of timing-based power level control systems described herein. By altering the amount of power by adjusting the timing profile of the carrier signal rather than the amplitude (e.g., the voltage) of the carrier signal in this way, significant flexibility may be achieved (power may be controlled using software and not requiring hardware updates) and burdensome design requirements (e.g., including a bulky buck converter and associated passive elements supporting the buck converter, etc.) may be reduced or eliminated.

Below carrier signal 500-1, FIG. 5 shows a fundamental component 504-1 associated with carrier signal 500-1 (implementing the first fundamental component described above in relation to carrier signal 106). Though carrier signal 500-1 may not be transmitted as output power within wireless transmission 310 (since it is the time-adjusted version of the carrier signal, time-adjusted carrier signal 500-2, that will be used as the output power), it will be understood that fundamental component 504-1 represents the fundamental component of carrier signal 500-1 that would result if this carrier signal were to be filtered down to its fundamental frequency (e.g., filtered to remove higher-level harmonic frequencies or overtones that give the square pulses their sharp rising and falling edges).

Similarly, below time-adjusted carrier signal 500-2, FIG. 5 shows a fundamental component 504-2 associated with time-adjusted carrier signal 500-2 (implementing the second fundamental component described above in relation to time-adjusted carrier signal 108). Since time-adjusted carrier signal 500-2 is to be used to carry output power within wireless transmission 310, fundamental component 504-2 may be transmitted as part of wireless transmission 310 after time-adjusted carrier signal 500-2 is filtered down to its fundamental frequency by an output filter (e.g., filtered to remove the higher-level harmonic frequencies or overtones that give the pulses their sharp rising and falling edges).

As shown, both fundamental components 504-1 and 504-2 share a same frequency 506 (represented by a time between successive peaks on the sinusoidal signal) and a same phase 508 (represented by a relative timing position of the peaks of the signals which does not shift one way or the other from fundamental component 504-1 to fundamental component 504-2). However, as further shown in FIG. 5, an amplitude 510 of fundamental component 504-1 is different from an amplitude 512 of fundamental component 504-2. This is due to the modifications to the timing profile of time-adjusted carrier signal 500-2 to reduce the duty cycle of certain pulses, to skip certain pulses, and so forth. Even though these modifications are made in a way that allows the fundamental frequency 506 and the fundamental phase 508 to be maintained, the amount of power carried by time-adjusted carrier signal 500-2 (represented by amplitude 512) is reduced from the maximum amount of power carried by carrier signal 500-1 (represented by amplitude 510).

As will now be described in more detail, the amount of output power provided on wireless transmission 310 (carried by time-adjusted carrier signal 500-2 and represented by amplitude 512) may be controlled with a great degree of precision and flexibility using a wide array of different timing profile patterns represented by different timing control datasets 314 that may be used. While it may not be possible to achieve every possible power level from the maximum supported power level (represented by amplitude 510) down to zero, a large number of discrete power levels (e.g., dozens or hundreds of potential power levels) may be achieved between the maximum supported power level and a power level of zero by leveraging different combinations and patterns of skipped pulses, shortened pulses, and so forth. These combinations and patterns may be stored as different timing control datasets 314 and may result in a wide array of different amplitudes 512 that range from amplitude 510 down to zero. Certain of these combinations and patterns will now be described in relation to FIGS. 6-9.

Figure 6:
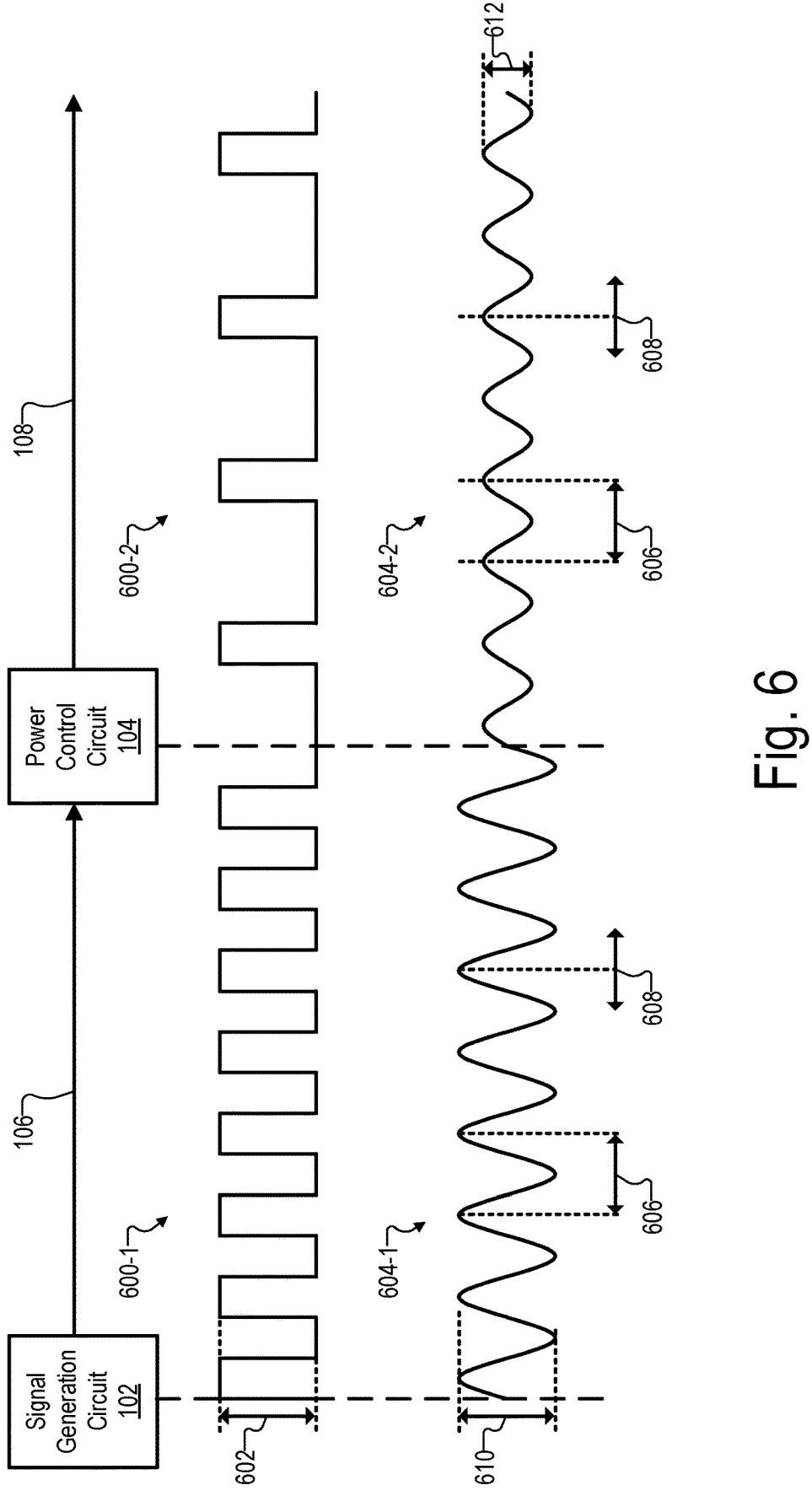

In FIG. 6, carrier signal 106 is implemented by a carrier signal 600-1, and time-adjusted carrier signal 108 is implemented by a time-adjusted carrier signal 600-2, both of which have a same amplitude 602. As with the example of FIG. 5, carrier signal 600-1 includes a series of pulses generated at a particular frequency, and the timing profile of the carrier signal is adjusted for the time-adjusted version of the carrier signal. Specifically, the timing profile of carrier signal 600-1 is adjusted in this example by skipping a sub-series of pulses from the series of pulses. The sub-series of pulses has a frequency lower than the particular frequency of carrier signal 600-1. For instance, as shown in this example, the sub-series of pulses that are skipped includes every other pulse, thus making the frequency of the sub-series half of the particular frequency in this example. It will be understood that in other examples (not shown), every third pulse, every fourth pulse, two out of every five pulses, or another suitable pattern of pulses may be skipped in the way illustrated for every other pulse in time-adjusted carrier signal 600-2.

Similarly as described above in relation to FIG. 5, a fundamental component 604-1 corresponding to carrier signal 600-1 is characterized by a frequency 606 and a phase 608 that are the same as the frequency and phase characterizing a fundamental component 604-2 corresponding to time-adjusted carrier signal 600-2. However, while fundamental component 604-1 is characterized by an amplitude 610 associated with a maximum power level, fundamental component 604-2 is characterized by an amplitude 612 that is less than amplitude 610 and is associated with a reduced power level (e.g., whatever power level is desired for a particular scenario as called for by target power level 308 in the ways described above). In this particular example in which every other pulse is skipped for time-adjusted carrier signal 600-2, for instance, the power level corresponding to amplitude 612 of fundamental component 604-2 may be approximately 25% of the power level corresponding to amplitude 610 of fundamental component 604-1.

Figure 7:
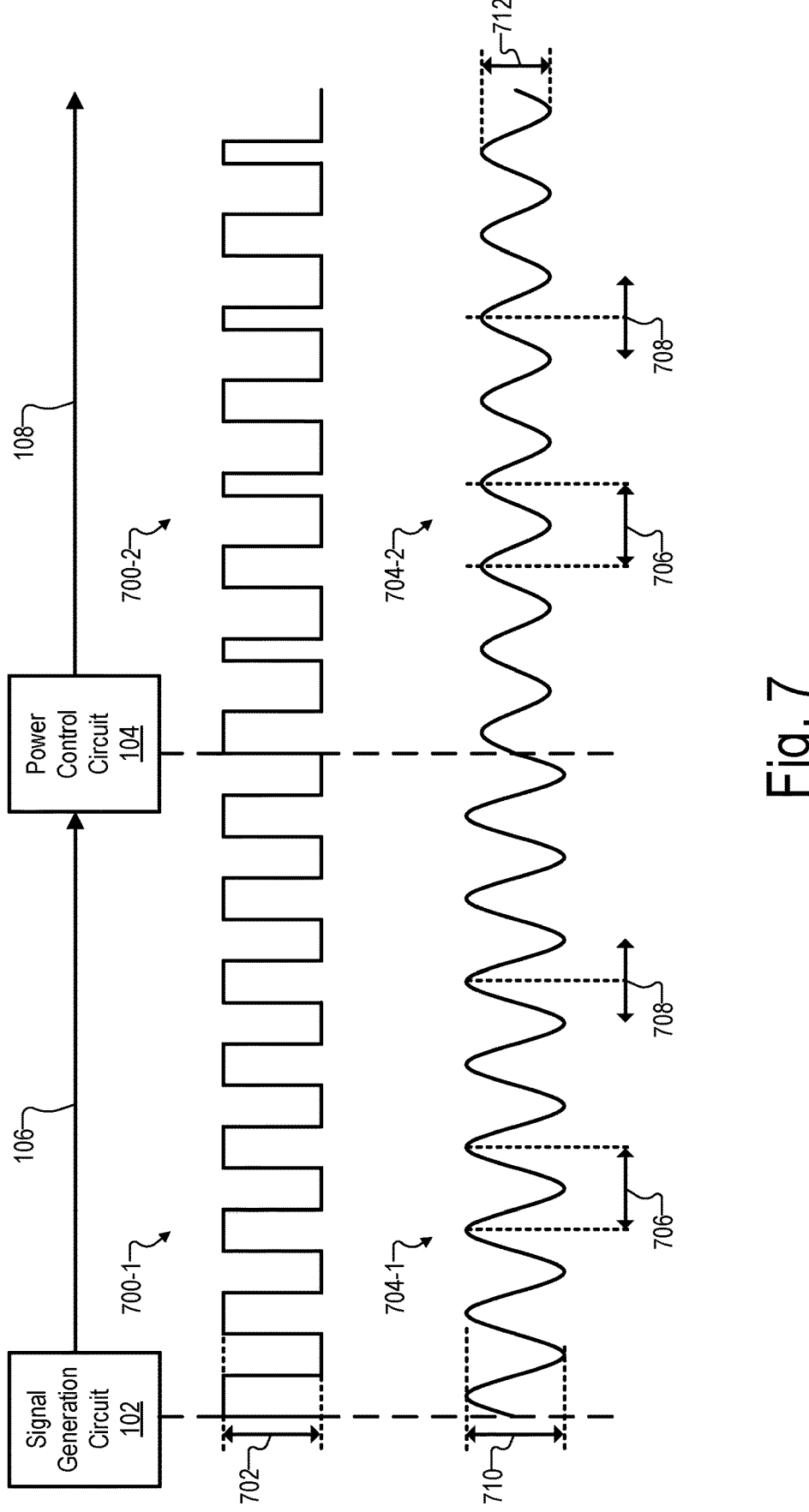

As another example, in FIG. 7 carrier signal 106 is implemented by a carrier signal 700-1, and time-adjusted carrier signal 108 is implemented by a time-adjusted carrier signal 700-2, both of which have a same amplitude 702. As with the examples of FIGS. 5-6, carrier signal 700-1 includes a series of pulses generated at a particular frequency, and the timing profile of the carrier signal is adjusted for the time-adjusted version of the carrier signal. Specifically, the timing profile of carrier signal 700-1 is adjusted in this example by symmetrically shortening a sub-series of pulses from the series of pulses. The sub-series of pulses symmetrically shortened may have a frequency lower than or equal to the particular frequency of carrier signal 700-1. For instance, as shown in this example, the sub-series of pulses that are symmetrically shortened includes every other pulse, thus making the frequency of the sub-series of pulses half of the particular frequency. It will be understood that in other examples (not shown), every third pulse, every fourth pulse, two out of every five pulses, or another suitable pattern of pulses may be symmetrically shortened in the way illustrated for every other pulse in time-adjusted carrier signal 700-2. In still other examples, every pulse could be symmetrically shortened, such that the frequency of the sub-series of pulses would be equal to the particular frequency of the series of pulses (rather than less than the particular frequency, as with the other examples mentioned).

Similarly as described above in relation to FIGS. 5-6, a fundamental component 704-1 corresponding to carrier signal 700-1 is characterized by a frequency 706 and a phase 708 that are the same as the frequency and phase characterizing a fundamental component 704-2 corresponding to time-adjusted carrier signal 700-2. However, while fundamental component 704-1 is characterized by an amplitude 710 associated with a maximum power level, fundamental component 704-2 is characterized by an amplitude 712 that is less than amplitude 710 and is associated with a reduced power level (e.g., whatever power level is desired for a particular scenario as called for by target power level 308 in the ways described above). It will be understood that even if amplitudes 610 and 710 are a same amplitude corresponding to a same maximum power level, amplitude 712 may be different from amplitude 612 since the different timing profiles applied to time-adjusted carrier signals 600-2 and 700-2 may correspond to different power levels of the large plurality of supported power levels described above.

Figure 8:
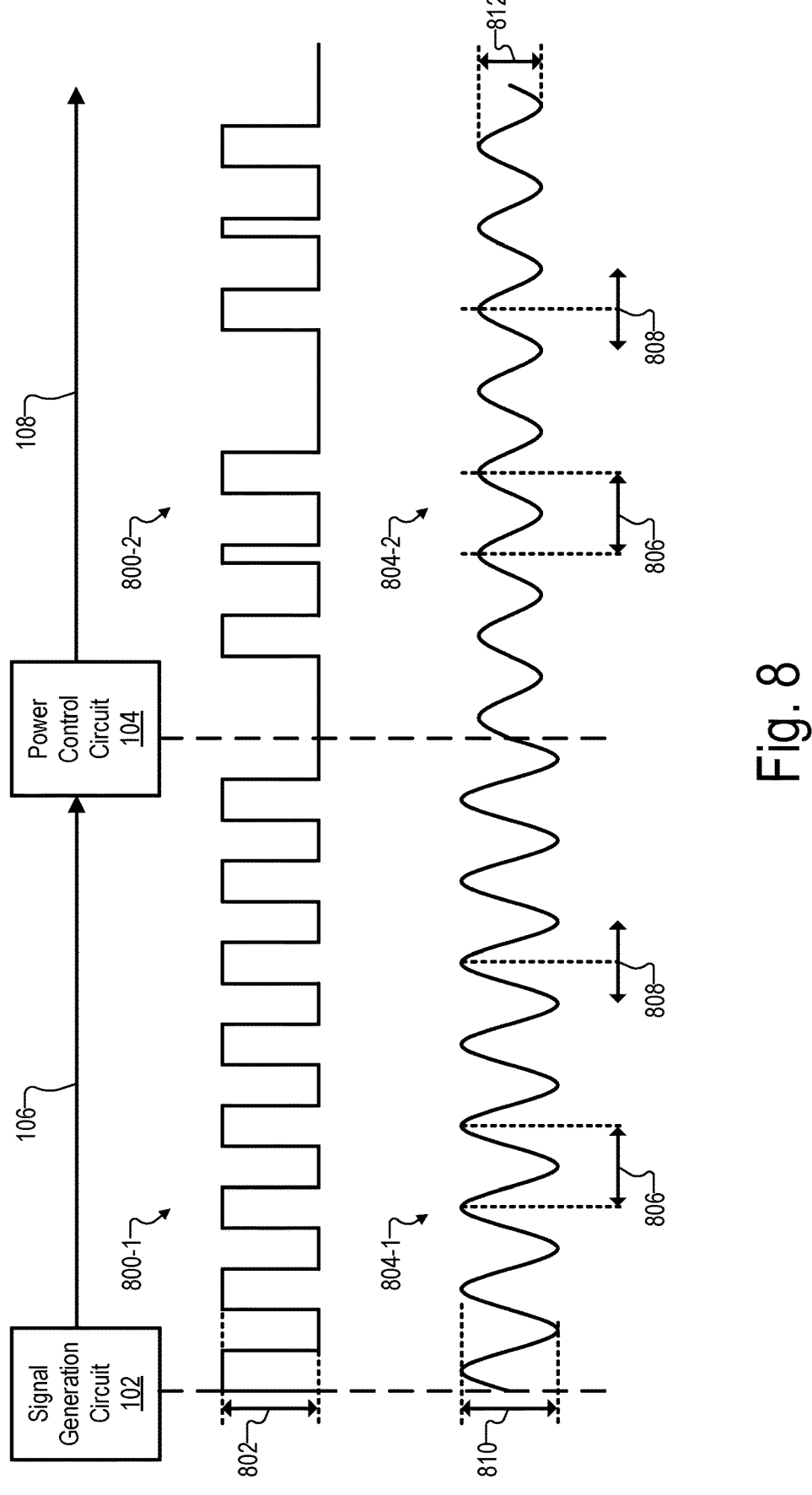

As yet another example, in FIG. 8 carrier signal 106 is implemented by a carrier signal 800-1, and time-adjusted carrier signal 108 is implemented by a time-adjusted carrier signal 800-2, both of which have a same amplitude 802. As with the examples of FIGS. 5-7, carrier signal 800-1 includes a series of pulses generated at a particular frequency, and the timing profile of the carrier signal is adjusted for the time-adjusted version of the carrier signal. Specifically, the timing profile of carrier signal 800-1 is adjusted in this example by a combination of skipping a first sub-series of pulses from the series of pulses, and symmetrically shortening a second sub-series of pulses from the series of pulses. The first sub-series of pulses that is skipped may have a first frequency lower than the particular frequency. For instance, as shown in this example, the first frequency of the first sub-series may be one-fourth the particular frequency such that every fourth pulse is skipped. The second sub-series of pulses may have a second frequency lower than or equal to a difference between the particular frequency of carrier signal 800-1 and the first frequency. For instance, as shown in this example, the second frequency of the second sub-series may be one-fourth the particular frequency such that every fourth pulse is shortened (a different pulse than the one that is skipped). In other examples, the second frequency of the second sub-series could be as high as three-fourths of the particular frequency such that three out of every four pulses (e.g., every pulse that is not skipped due to being part of the first sub-series) are shortened. As has been described, various other patterns of skipped and symmetrically shortened pulses may be implemented in similar ways as illustrated for time-adjusted carrier signal 800-2. In all of these examples, it will be understood that the first and second sub-series of pulses are non-overlapping such that each pulse is either skipped, shortened, or left unmodified (but not more than one of these).

Similarly as described above in relation to FIGS. 5-7, a fundamental component 804-1 corresponding to carrier signal 800-1 is characterized by a frequency 806 and a phase 808 that are the same as the frequency and phase characterizing a fundamental component 804-2 corresponding to time-adjusted carrier signal 800-2. However, while fundamental component 804-1 is characterized by an amplitude 810 associated with a maximum power level, fundamental component 804-2 is characterized by an amplitude 812 that is less than amplitude 810 and is associated with a reduced power level (e.g., whatever power level is desired for a particular scenario as called for by target power level 308 in the ways described above). It will be understood that even if amplitudes 610, 710, and 810 are a same amplitude corresponding to a same maximum power level, amplitudes 612, 712, and 812 may be different from one another since the different timing profiles applied to time-adjusted carrier signals 600-2, 700-2, and 800-2 may correspond to different power levels of the large plurality of supported power levels described above.

Figure 9:
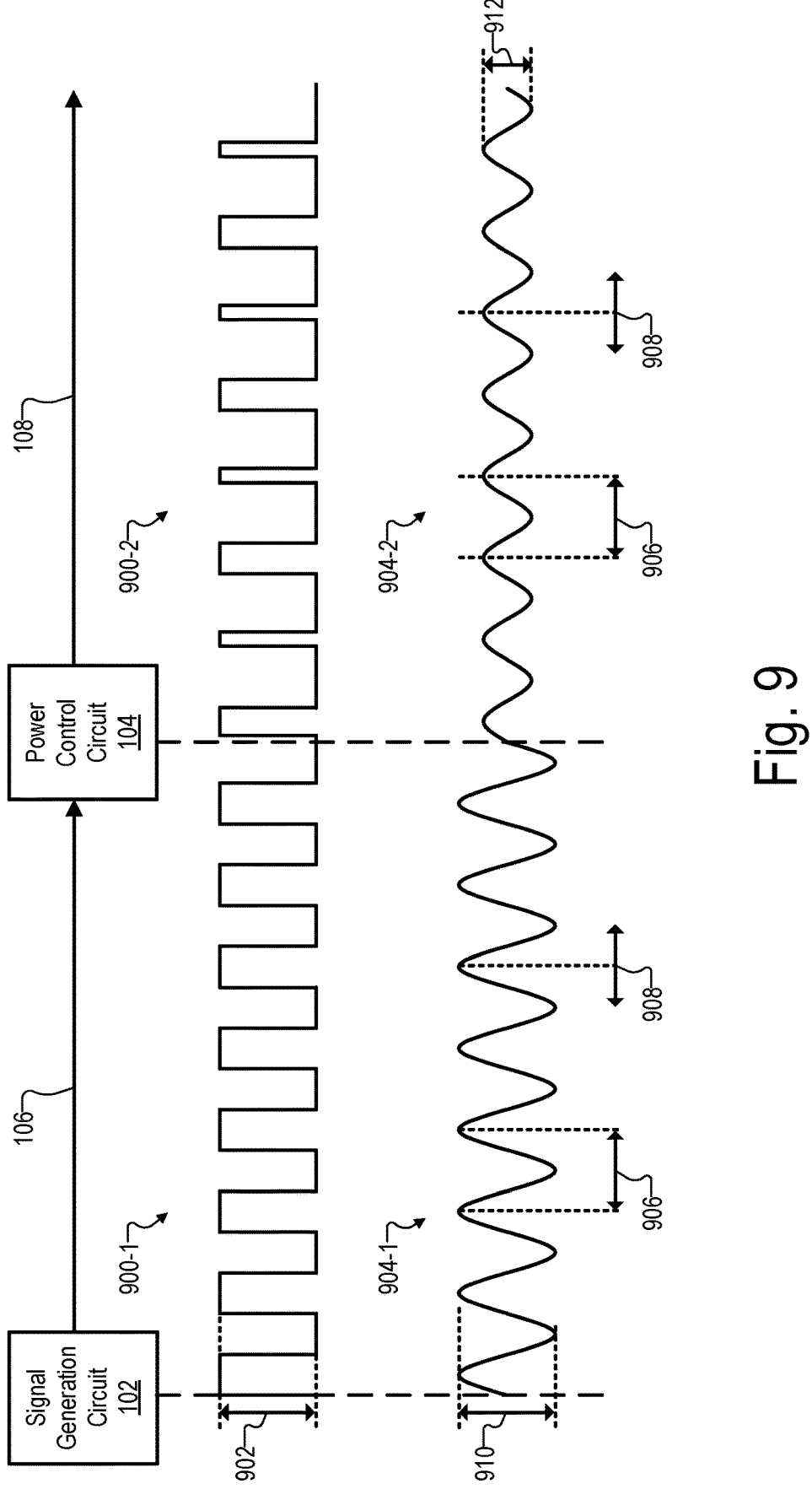

As yet another example, in FIG. 9 carrier signal 106 is implemented by a carrier signal 900-1, and time-adjusted carrier signal 108 is implemented by a time-adjusted carrier signal 900-2, both of which have a same amplitude 902. As with the examples of FIGS. 5-8, carrier signal 900-1 includes a series of pulses generated at a particular frequency, and the timing profile of the carrier signal is adjusted for the time-adjusted version of the carrier signal. Specifically, the timing profile of carrier signal 900-1 is adjusted in this example by a combination of symmetrically shortening a first sub-series of pulses from the series of pulses by a first amount and symmetrically shortening a second sub-series of pulses from the series of pulses by a second amount distinct from the first amount. The first sub-series of pulses shortened by the first amount may have a first frequency lower than the particular frequency of carrier signal 900-1. For instance, as shown in this example, the first frequency of the first sub-series may be one-half the particular frequency such that every other pulse is shortened by a first amount (e.g., a relatively small amount such that these pulses are only slightly narrower than the pulses of carrier signal 900-1). The second sub-series of pulses shortened by the second amount may have a second frequency that is also lower than the particular frequency of carrier signal 900-1. For instance, as shown in this example, the second frequency of the second sub-series may also be one-half the particular frequency so that pulses shortened by shortened by the second amount (e.g., a relatively large amount such that these pulses are more significantly narrower than the pulses of carrier signal 900-1) are interleaved with the pulses of the first sub-series. Various other patterns of skipped and symmetrically shortened pulses of varying pulse widths may be implemented in similar ways as illustrated for time-adjusted carrier signal 900-2. In all of these examples, it will be understood that various sub-series of pulses may be non-overlapping such that each pulse is either skipped, shortened by one amount or another, or left unmodified.

Similarly as described above in relation to FIGS. 5-8, a fundamental component 904-1 corresponding to carrier signal 900-1 is characterized by a frequency 906 and a phase 908 that are the same as the frequency and phase characterizing a fundamental component 904-2 corresponding to time-adjusted carrier signal 900-2. However, while fundamental component 904-1 is characterized by an amplitude 910 associated with a maximum power level, fundamental component 904-2 is characterized by an amplitude 912 that is less than amplitude 910 and is associated with a reduced power level (e.g., whatever power level is desired for a particular scenario as called for by target power level 308 in the ways described above). It will be understood that even if amplitudes 610, 710, 810, and 910 are a same amplitude corresponding to a same maximum power level, amplitudes 612, 712, 812, and 912 may be different from one another since the different timing profiles applied to time-adjusted carrier signals 600-2, 700-2, 800-2, and 900-2 may correspond to different power levels of the large plurality of supported power levels described above.

As has been mentioned, wireless transmission 310 may be used to deliver not only power, but also data from an external component of a medical system (e.g., external component 302) to an internal component (e.g., internal component 304). For example, output data based on input data provided to apparatus 100 may be delivered to the internal component by being modulated onto the time-adjusted version of the carrier signal that is being transmitted in wireless transmission 310 (e.g., time-adjusted carrier signal 108 or an implementation thereof such as time-adjusted carrier signal 500-2, 600-2, 700-2, 800-2, or 900-2).

To include such output data within wireless transmission 310, apparatus 100 (e.g., power control circuit 104 within apparatus 100) may be configured to generate time-adjusted carrier signal 108 in a manner that modulates the output data onto time-adjusted carrier signal 108 by causing the second fundamental component (i.e., the fundamental component of time-adjusted carrier signal 108) to have different amplitudes at different times. Specifically, for a first binary value of the output data (e.g., a 'HIGH' value, a '1' value, etc.), the second fundamental component may have the second amplitude associated with the target power level (e.g., any of amplitudes 512, 612, 712, 812, or 912, or another suitable amplitude from the plurality of potential amplitudes attainable using the different timing profiles described above). Then, for a second binary value of the output data (e.g., a 'LOW' value, a '0' value, etc.), the second fundamental component may have a third amplitude lower than the second amplitude associated with the target power level. For instance, as will now be described and illustrated, this third amplitude may be an amplitude of zero to implement an On-Off Keying (OOK) modulation protocol, or may be a non-zero amplitude such as a different one of amplitudes 512, 612, 712, 812, or 912 (or another suitable amplitude from the plurality of potential amplitudes attainable using the different timing profiles described above) to implement an Amplitude Shift Keying (ASK) modulation protocol.

Figure 10:
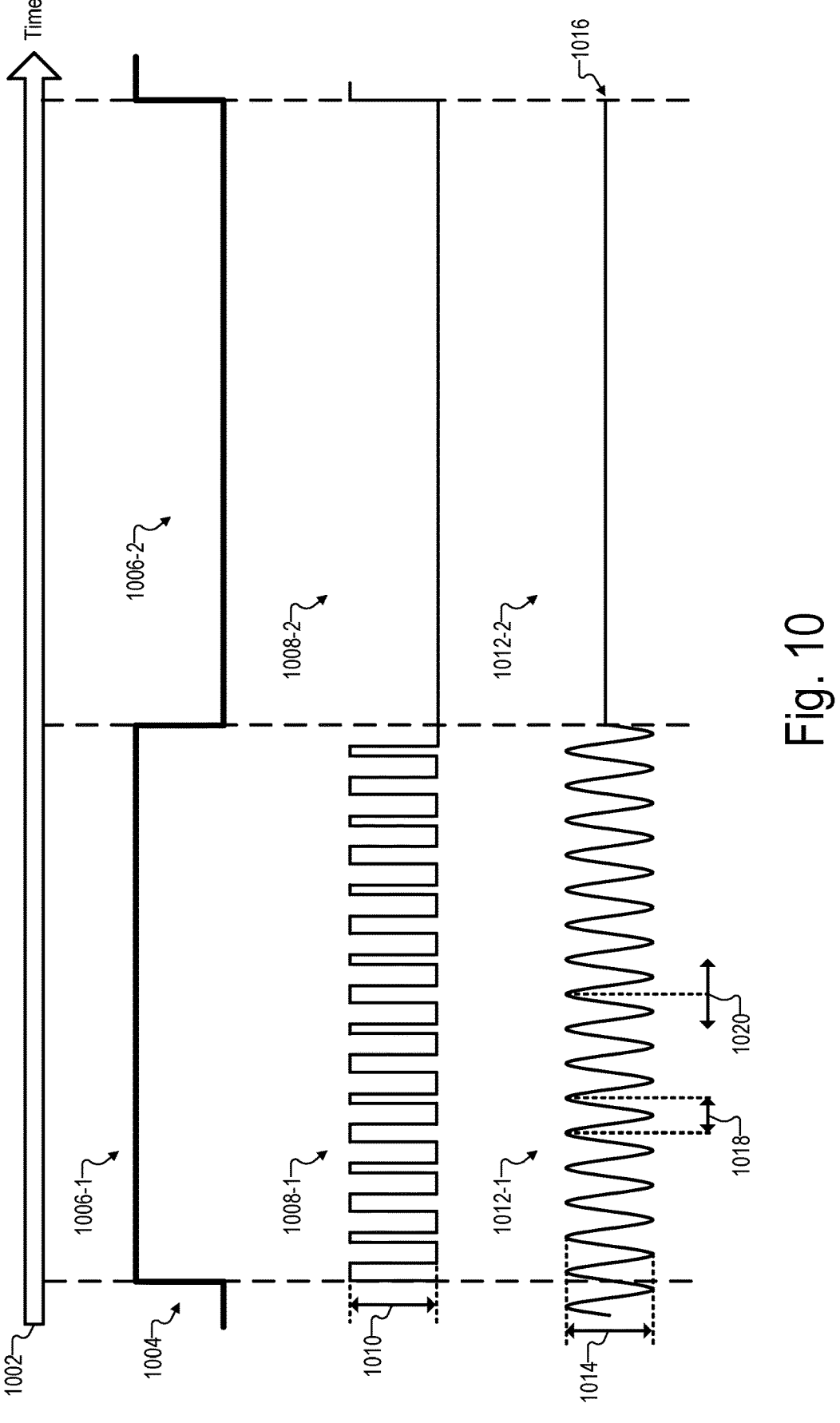
FIGS. 10-11 show illustrative ways that data may be modulated onto a carrier signal for wireless transmission in accordance with timing-based power level control implementations described herein.
Figure 11:
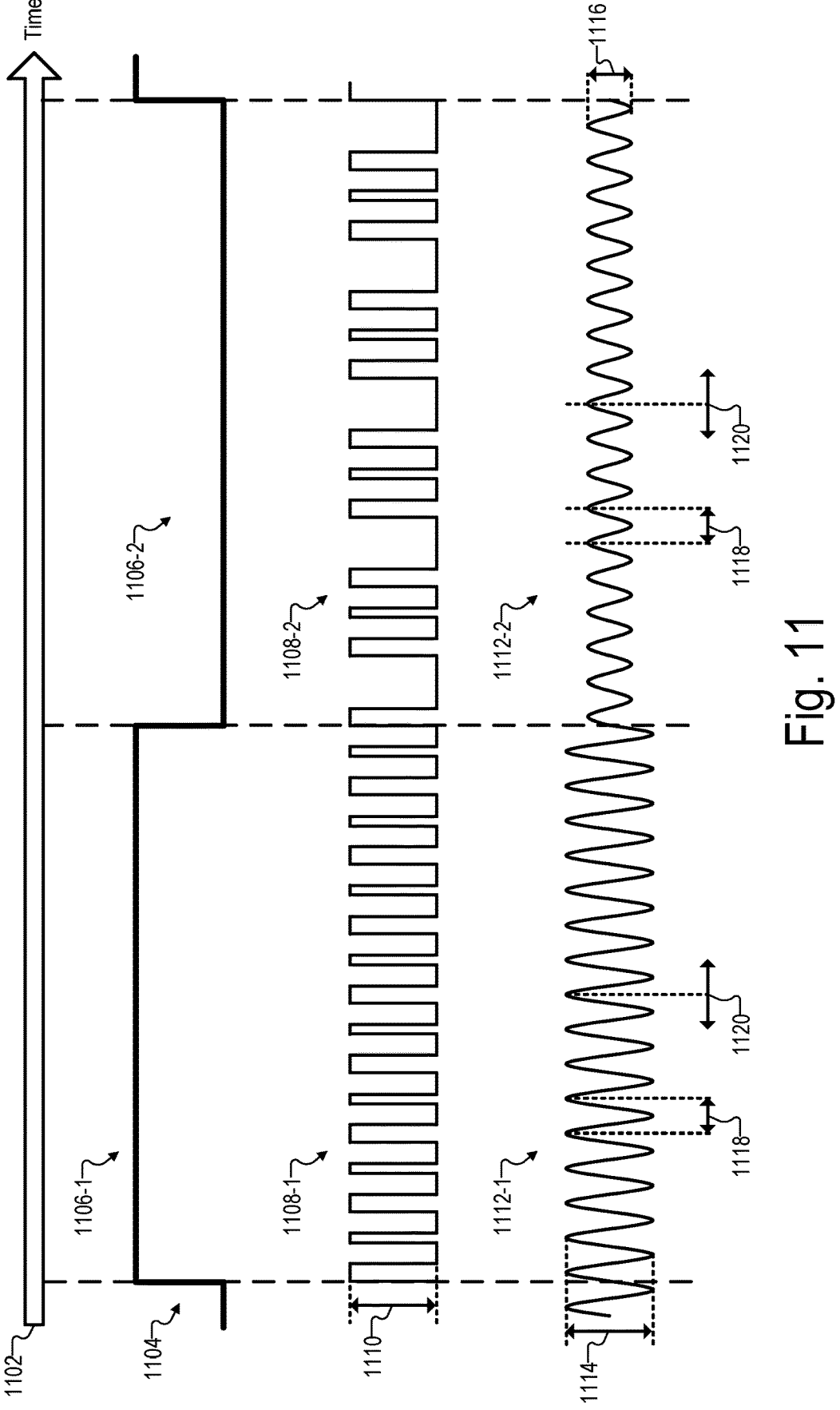

To illustrate, FIGS. 10-11 show illustrative ways that output data may be modulated onto a carrier signal (e.g., a time-adjusted version of the carrier signal) for wireless transmission of power in accordance with timing-based power level control implementations described herein. Specifically, FIG. 10 shows an implementation employing an OOK modulation protocol while FIG. 11 shows an implementation employing an ASK modulation protocol.

Referring first to FIG. 10, various waveforms are shown in relation to a timeline 1002. For example, a data waveform 1004 is shown to include different binary values 1006 such as a HIGH binary value 1006-1 (representing a binary '1') and a LOW binary value 1006-2 (representing a binary '0'). Drawn below binary values 1006 are different versions of a time-adjusted carrier signal 1008. Specifically, a first time-adjusted carrier signal 1008-1 is shown to have a first amplitude 1010 and to include a series of pulses that may comport with any of the timing profiles described herein (e.g., including skipped, shortened, unmodified, and/or other pulses as may serve a particular implementation). As shown, a fundamental component 1012-1 corresponding to time-adjusted carrier signal 1008-1 is shown to have a particular amplitude 1014 that is associated with a power level carried by time-adjusted carrier signal 1008-1 while data waveform 1004 carries the HIGH binary value 1006-1, as well as a particular frequency 1018 and a particular phase 1020.

Because FIG. 10 illustrates an OOK modulation protocol, when data waveform 1004 carries the LOW binary value 1006-2, a second time-adjusted carrier signal 1008-2 is shown to have an amplitude of 0. In other words, in the On-Off Keying modulation protocol, the carrier signal is completely shut off while transmitting a LOW binary value 1006-2 and a fundamental component 1012-2 corresponding to the zero-amplitude time-adjusted carrier signal 1008-2 is likewise shown to have an amplitude 1016 of zero, corresponding to a power level of zero. Hence, in this OOK modulation example, the third amplitude (amplitude 1016) is implemented as an amplitude of zero that is used within the OOK modulation protocol to implement the modulating of the output data onto the time-adjusted version of the carrier signal.

In contrast, FIG. 11 illustrates an example in which the third amplitude is a non-zero amplitude (e.g., an amplitude associated with an additional timing profile of the carrier signal distinct from the timing profile used to cause the second fundamental component of the original carrier signal to have the second amplitude) used within an ASK modulation protocol to implement the modulating of the output data onto the time-adjusted version of the carrier signal. Similar to FIG. 10, FIG. 11 shows various waveforms in relation to a timeline 1102. For example, a data waveform 1104 is shown to include different binary values 1106 such as a HIGH binary value 1106-1 (representing a binary '1') and a LOW binary value 1106-2 (representing a binary '0'). Drawn below binary values 1106 are different versions of a time-adjusted carrier signal 1108. Specifically, a first time-adjusted carrier signal 1108-1 is shown to have a first amplitude 1110 and to include a series of pulses that may comport with any of the timing profiles described herein (e.g., including skipped, shortened, unmodified, and/or other pulses as may serve a particular implementation). As shown, a fundamental component 1112-1 corresponding to time-adjusted carrier signal 1108-1 is shown to have a particular amplitude 1114 that is associated with a power level carried by time-adjusted carrier signal 1108-1 while data waveform 1104 carries the HIGH binary value 1106-1, as well as a particular frequency 1118 and a particular phase 1120.

Because FIG. 11 illustrates an ASK modulation protocol, when data waveform 1104 carries the LOW binary value 1106-2, a second time-adjusted carrier signal 1108-2 is shown to have the same amplitude 1110, but to employ a different timing protocol (e.g., a timing protocol in which more pulses are skipped or shortened, etc.). As such, for this Amplitude-Shift Keying modulation protocol, the carrier signal is remains active while transmitting a LOW binary value 1106-2, but uses a different timing protocol (e.g., associated with a different timing control dataset 314) such that a fundamental component 1112-2 corresponding to the time-adjusted carrier signal 1108-2 is shown to have an amplitude 1116 that is non-zero, but is lower than amplitude 1114. Amplitude 1116 may correspond to a power level lower than the power level associated with amplitude 1114.

As mentioned above, maintaining the frequency and phase of the fundamental component of a carrier signal while reducing the amplitude may be performed by adjusting the duty cycle of a pulse in a manner referred to herein as symmetrically shortening the pulse. This duty cycle adjustment moves rising and falling edges of a pulse symmetrically inward toward one another in a manner that maintains the timing of zero crossings of the fundamental component so as to maintain the phase as has been described and illustrated. Symmetric shortening of the pulses of a carrier signal may be achieved in any suitable way. For instance, in one implementation, power control circuit 104 may include a delay circuit (e.g., a voltage-controlled delay line circuit, etc.) that inputs the carrier signal and outputs an array of delayed versions of the carrier signal. Power control circuit 104 may then be configured to generate the time-adjusted version of the carrier signal by performing certain operations such as the following. Power control circuit 104 may select a first delayed version and a second delayed version of the carrier signal from the array of delayed versions of the carrier signal. For instance, the first and second delayed versions may be selected based on the timing control data (e.g., whatever signals are indicated by an identified timing control dataset 314 for a given target power level 308). Power control circuit 104 may then generate the time-adjusted version of the carrier signal based on the selected first and second delayed versions of the carrier signal. For example, power control circuit 104 may use logic to create a rising edge on the time-adjusted carrier signal for each rising edge of the first delayed version of the carrier signal and to create a falling edge on the time-adjusted carrier signal for each falling edge of the second delayed version of the carrier signal.

Figure 12:
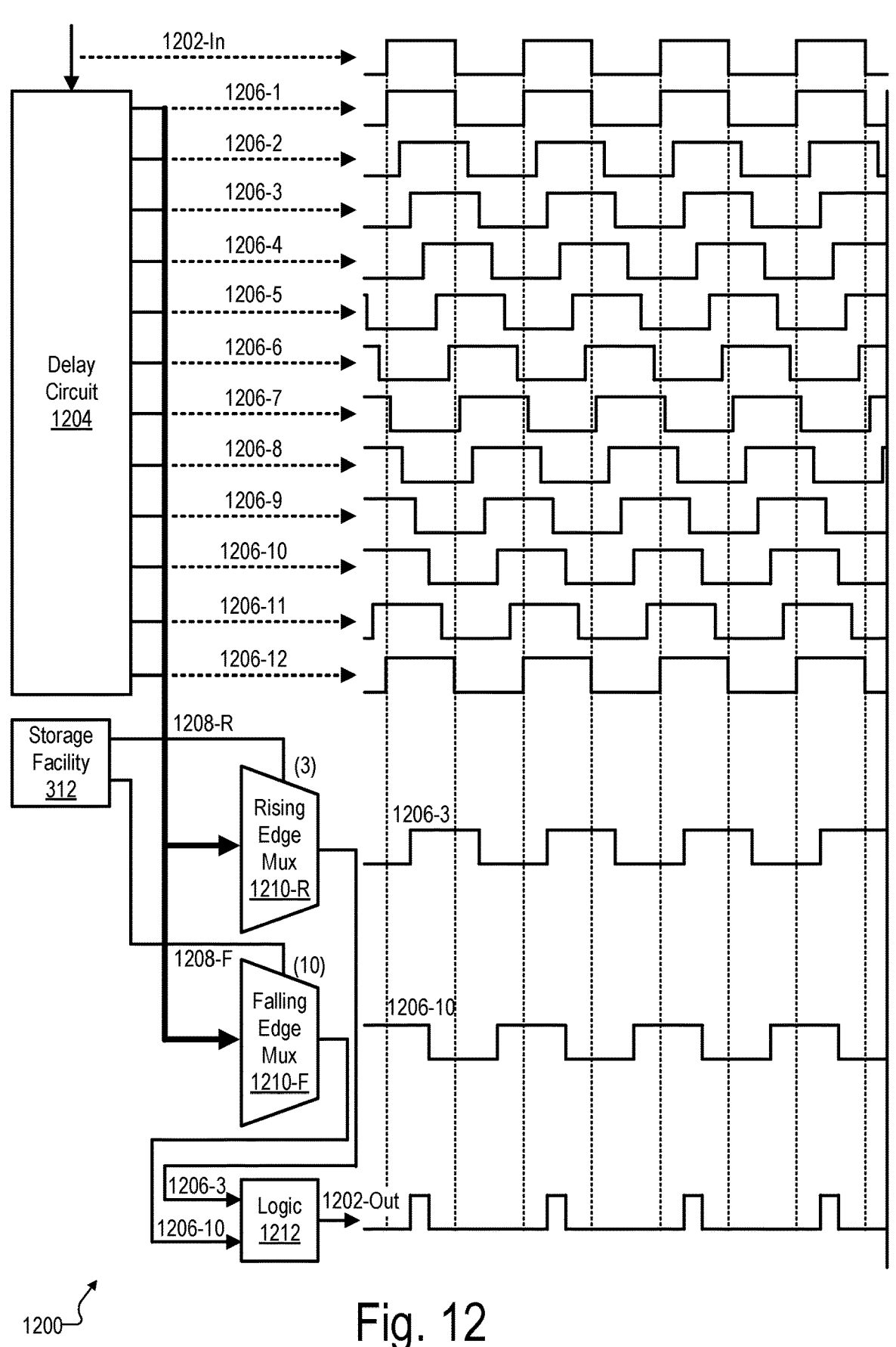
FIG. 12 shows certain aspects of one illustrative way in which a time-adjusted version of a carrier signal may be generated for use within timing-based power level control implementations described herein.

To illustrate, FIG. 12 shows certain aspects of this particular way of generating the time-adjusted version of the carrier signal for use within timing-based power level control implementations described herein. It will be understood that the manner of symmetrically shortening pulses of a carrier signal described above and shown in FIG. 12 are not the only ways that symmetric shortening of a series of pulses may be performed and that various other ways may be used as an alternative to the novel technique shown. Additionally, it will be understood that, while FIG. 12 shows a technique for generating a time-adjusted carrier signal in which every pulse is symmetrically shortened by the same amount, related techniques or other techniques may be employed to implement some of the other timing profiles described herein (e.g., in which only some but not all of the pulses are shortened, in which different pulses are shortened by different amounts, in which certain pulses are skipped, etc.). For instance, one way of implementing a more complex timing profile may be to duplicate the technique of FIG. 12 to generate a variety of intermediate time-adjusted carrier signals in which the pulses are shortened by different amounts, and then multiplexing these intermediate signals together according to certain timing parameters so as to generate a final time-adjusted carrier signal (e.g., a signal that shortens different pulses by different amounts in accordance with a desired timing profile). In some examples, a zero-amplitude signal (e.g., ground) may also be multiplexed together to add skipped pulses to the timing profile as may serve a particular implementation.

In accordance with the description above, FIG. 12 shows a symmetric pulse shortening circuit 1200 that inputs a carrier signal 1202-In and outputs a time-adjusted version of the carrier signal referred to as time-adjusted carrier signal 1202-Out. It will be understood that time-adjusted carrier signal 1202-Out may correspond to time-adjusted carrier signal 108 in certain scenarios or may serve as an intermediary signal to generate an implementation of time-adjusted carrier signal 108 in other examples (as has been described).

To generate time-adjusted carrier signal 1202-Out based on carrier signal 1202-In, circuit 1200 includes a delay circuit 1204 that takes in carrier signal 1202-In and outputs a plurality of delayed versions of carrier signal 1202-In referred to as delayed carrier signals 1206. In this example, twelve delayed carrier signals 1206 are shown (i.e., delayed carrier signals 1206-1 through 1206-12), but it will be understood that twelve is only an example and other implementations may provide more or fewer delayed carrier signals 1206 to achieve a desired amount of resolution. A delay circuit used to implement delay circuit 1204 may be fully compatible with integrated circuits and may be made controllable through an adjustable bias current, or an adjustable capacitive load such as with a varactor. Delay circuit 1204 may be further calibrated using an available time base with a delay-locked loop (DLL). For example, a DLL with a digitally programmable voltage-controlled delay line (VCDL) may be used to calibrate the delay elements of a delay line, and then replica delay lines may be used to digitally select the length of the line and adjust the delay of each element to generate pulse start and stop signals corresponding to the desired duty cycle (or pulse width), and time shift for driving an RF transmitter.

As shown, delayed carrier signals 1206 are delayed by amounts that are evenly distributed along the period of carrier signal 1202-In so as to create twelve copies of the carrier signal that have different phases evenly distributed between 0° and 360° (a full cycle of the carrier signal). Control data 1208 may be accessed from storage facility 312 for use by two multiplexors 1210 to select two of delayed carrier signals 1206. For instance, a particular timing control dataset 314 stored in storage facility 312 may include data indicative of first control data 1208-R indicative of one of delayed carrier signals 1206 (e.g., signal 1206-3 in this example, as indicated by the "(3)" in FIG. 12) that is to control the rising edge of time-adjusted carrier signal 1202-Out, as well as second control data 1208-F indicative of a different one of delayed carrier signals 1206 (e.g., signal 1206-10 in this example, as indicated by the "(10)" in FIG. 12) that is to control the falling edge of time-adjusted carrier signal 1202-Out. Accordingly, as shown, a rising edge multiplexor (mux) 1210-R controlled by control data 1208-R is shown to output delayed carrier signal 1206-3, while a falling edge multiplexor (mux) 1210-F controlled by control data 1208-F is shown to output delayed carrier signal 1206-10.

It is noted that timing control data 1208 may be preconfigured so as to always select delayed carrier signals that are symmetrically related so as to ensure that pulses of time-adjusted carrier signal 1202-Out will be symmetrically shortened pulses corresponding to the pulses of carrier signal 1202-In (and thereby maintain the same phase for the fundamental component, as has been described). For example, instead of delayed carrier signals 1206-3 and 1206-10, a different timing control dataset 314 (i.e., different timing control data 1208) accessed from storage facility 312 may select delayed carrier signals 1206-2 and 1206-11, or 1206-4 and 1206-9, or 1206-5 and 1206-8, or another such symmetrical pair as may serve a particular implementation.

Logic 1212 may input the selected delayed carrier signals 1206 (e.g., delayed carrier signals 1206-3 and 1206-10 in this example) and combine them to form time-adjusted carrier signal 1202-Out in any suitable way. For instance, in this example, logic 1212 may be implemented by an AND gate, since time-adjusted carrier signal 1202-Out is shown to be HIGH when delayed carrier signals 1206-3 and 1206-10 are both HIGH and to be LOW otherwise. In other examples, other logic could be implemented such as to invert (NOT) the delayed carrier signal 1206 coming from falling edge multiplexor 1210-F (e.g., signal 1206-3) prior to its entry into an AND gate with the delayed carrier signal 1206 coming from rising edge multiplexor 1210-R (e.g., signal 1206-10). In this way, it would be the rising edge (rather than the falling edge) of delayed carrier signal 1206-10 that would instigate the falling edge of time-adjusted carrier signal 1202-Out and the pulses of time-adjusted carrier signal 1202-Out would have a different pulse width (as well as a different phase from carrier signal 1202-In, though different time-adjusted carrier signals 1202-Out generated in this way for an ASK modulation protocol would have the same phase as one another such that wireless transmission 310 would maintain a consistent phase). In still other examples, other logic may be utilized such as a set/reset (SR) latch or flip-flop or other suitable logic configured to combine the selected delayed carrier signals 1206 to generate time-adjusted carrier signal 1202-Out in any manner as may serve a particular implementation.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:

a signal generation circuit configured to generate a carrier signal for wireless transmission of output power and output data, the carrier signal associated with a first fundamental component having a particular frequency, a particular phase, and a first amplitude associated with a maximum supported power level for the output power; and a power control circuit configured to generate, based on timing control data corresponding to a target power level for the output power that is lower than the maximum supported power level for the output power, a time-adjusted version of the carrier signal that maintains an amplitude of the carrier signal and adjusts a timing profile of the carrier signal such that a second fundamental component associated with the time-adjusted version of the carrier signal has the particular frequency, the particular phase, and a second amplitude lower than the first amplitude and associated with the target power level for the output power; wherein:

the carrier signal includes a series of pulses generated at the particular frequency; and the timing profile of the carrier signal is adjusted for the time-adjusted version of the carrier signal by at least one of:

skipping a first sub-series of pulses from the series of pulses, the first sub-series of pulses having a first frequency lower than the particular frequency, or symmetrically shortening a second sub-series of pulses from the series of pulses, the second sub-series of pulses having a second frequency lower than or equal to the particular frequency.

2. The apparatus of claim 1, wherein:

the second frequency is lower than or equal to a difference between the particular frequency and the first frequency; and the first and second sub-series of pulses are non-overlapping.

3. The apparatus of claim 1, implemented within an external headpiece included in a cochlear implant system; wherein the cochlear implant system further includes an internal cochlear implant configured to receive the wireless transmission of output power and output data from the external headpiece when the internal cochlear implant is implanted within a recipient of the cochlear implant system and the external headpiece is external to the recipient.

4. The apparatus of claim 3, wherein the external headpiece is an integrated headpiece that includes, together with the signal generation circuit and the power control circuit, a sound processing circuit configured to generate, based on input audio data, the output data wirelessly transmitted to the internal cochlear implant by way of the wireless transmission.

5. The apparatus of claim 1, wherein the power control circuit is configured to generate the time-adjusted version of the carrier signal in a manner that modulates the output data onto the time-adjusted version of the carrier signal by causing the second fundamental component to have:

for a first binary value of the output data, the second amplitude associated with the target power level; and for a second binary value of the output data, a third amplitude lower than the second amplitude associated with the target power level.

6. The apparatus of claim 5, wherein:

the third amplitude is a non-zero amplitude used within an amplitude shift keying (ASK) modulation protocol to implement the modulating of the output data onto the time-adjusted version of the carrier signal; and the third amplitude is associated with an additional timing profile of the carrier signal distinct from the timing profile of the carrier signal that causes the second fundamental component to have the second amplitude.

7. The apparatus of claim 5, wherein the third amplitude is an amplitude of zero that is used within an on-off keying (OOK) modulation protocol to implement the modulating of the output data onto the time-adjusted version of the carrier signal.

8. The apparatus of claim 1, wherein:

the power control circuit includes a delay circuit that inputs the carrier signal and outputs an array of delayed versions of the carrier signal; and the power control circuit is configured to generate the time-adjusted version of the carrier signal by:

selecting, based on the timing control data and from the array of delayed versions of the carrier signal, a first delayed version and a second delayed version of the carrier signal, and generating, based on the selected first and second delayed versions of the carrier signal, the time-adjusted version of the carrier signal.

9. The apparatus of claim 1, further comprising a storage facility configured to maintain a plurality of timing control datasets corresponding to a plurality of different target power levels for the output power;

wherein:

the plurality of timing control datasets includes a particular timing control dataset for the timing control data corresponding to the target power level, and as part of the generating of the time-adjusted version of the carrier signal, the power control circuit selects and accesses the particular timing control dataset from the storage facility.

10. The apparatus of claim 9, implemented within an external component that is included within a medical system that further includes an internal component configured to receive the wireless transmission of output power and output data from the external component when the internal component is implanted within a recipient of the medical system and the external component is external to the recipient;

wherein:

prior to the selecting and accessing of the particular timing control dataset and as further part of the generating of the time-adjusted version of the carrier signal, the power control circuit identifies the target power level for the output power based on at least one of:

a program strategy used for the wireless transmission of output power and output data, or a distance between the external and internal components of the medical system when the internal component is implanted within the recipient and the external component is external to the recipient; and the power control circuit selects and accesses the particular timing control dataset from the storage facility based on the identified target power level.

11. The apparatus of claim 9, further comprising a battery monitor circuit that continuously or periodically detects a battery level of a battery supplying power to the signal generation circuit and the power control circuit;

wherein:

the power control circuit is configured to generate the time-adjusted version of the carrier signal based on the timing control data when the battery monitor circuit detects that the battery level is above a threshold, and the power control circuit is configured to generate the time-adjusted version of the carrier signal based on different timing control data corresponding to a different target power level for the output power when the battery monitor circuit detects that the battery level is below the threshold.

12. A cochlear implant system comprising:

a headpiece configured to be worn externally by a recipient of the cochlear implant system and to provide a wireless transmission of output power and output data;

a cochlear implant configured to be implanted within the recipient and to receive the wireless transmission from the headpiece;

a signal generation circuit included within the headpiece and configured to generate a carrier signal for the wireless transmission, the carrier signal associated with a first fundamental component having a particular frequency, a particular phase, and a first amplitude associated with a maximum supported power level for the output power; and a power control circuit included within the headpiece and configured to generate, based on timing control data corresponding to a target power level for the output power that is lower than the maximum supported power level for the output power, a time-adjusted version of the carrier signal that maintains an amplitude of the carrier signal and adjusts a timing profile of the carrier signal such that a second fundamental component associated with the time-adjusted version of the carrier signal has the particular frequency, the particular phase, and a second amplitude lower than the first amplitude and associated with the target power level for the output power; wherein:

the carrier signal includes a series of pulses generated at the particular frequency; and the timing profile of the carrier signal is adjusted for the time-adjusted version of the carrier signal by at least one of:

skipping a first sub-series of pulses from the series of pulses, the first sub-series of pulses having a first frequency lower than the particular frequency, or symmetrically shortening a second sub-series of pulses from the series of pulses, the second sub-series of pulses having a second frequency lower than or equal to the particular frequency.

13. The cochlear implant system of claim 12, wherein:

the second frequency is lower than or equal to a difference between the particular frequency and the first frequency; and the first and second sub-series of pulses are non-overlapping.

* * * * *